United States Patent
Kelly et al.

(10) Patent No.: US 7,462,637 B2
(45) Date of Patent: *Dec. 9, 2008

(54) DERIVATIVES OF [6,7-DIHYDRO-5H-IMIDAZO[1,2-A]IMIDAZOLE-3-SULFONYL]-PYRROLIDINE-2-CARBOXYLIC ACID AMIDE

(75) Inventors: Terence A. Kelly, Ridgefield, CT (US); Jin Mi Kim, Sandy Hook, CT (US); René Marc Lemieux, Plantsville, CT (US); Matt Aaron Tschantz, Newtown, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 455 days.

This patent is subject to a terminal disclaimer.

(21) Appl. No.: 10/969,698

(22) Filed: Oct. 20, 2004

(65) Prior Publication Data

US 2005/0054704 A1    Mar. 10, 2005

Related U.S. Application Data

(62) Division of application No. 10/685,638, filed on Oct. 15, 2003, now Pat. No. 6,852,748.

(60) Provisional application No. 60/422,449, filed on Oct. 30, 2002.

(51) Int. Cl.
*A61K 31/4188* (2006.01)
*A61K 31/5375* (2006.01)
*C07D 235/02* (2006.01)
*C07D 403/12* (2006.01)

(52) U.S. Cl. .............. 514/387; 548/301.7; 548/302.7; 548/303.1; 546/152; 546/168; 546/268.4; 546/273.1; 544/106; 544/139; 544/242; 544/335; 514/231.5; 514/256; 514/311

(58) Field of Classification Search .............. 548/300.1, 548/301.7, 302.7, 303.1; 514/385, 387
See application file for complete search history.

(56) References Cited

U.S. PATENT DOCUMENTS

| | | | |
|---|---|---|---|
| 6,355,664 B1 | 3/2002 | Kelly et al. | |
| 6,492,408 B1 | 12/2002 | Wu et al. | |
| 6,689,804 B2 | 2/2004 | Wu et al. | |
| 6,844,360 B2 * | 1/2005 | Kelly et al. | 514/387 |
| 6,852,748 B1 * | 2/2005 | Kelly et al. | 514/387 |

FOREIGN PATENT DOCUMENTS

| | | |
|---|---|---|
| WO | WO 98/39303 A1 | 9/1998 |
| WO | WO 01/07440 A1 | 2/2001 |

\* cited by examiner

*Primary Examiner*—Golam M Shameem
(74) *Attorney, Agent, or Firm*—Michael P. Morris; Mary-Ellen M. Devlin; Philip I. Datlow

(57) ABSTRACT

Derivatives of 6,7-dihydro-5H-imidazo[1,2-a]imidazole-3-sulfonyl]-pyrrolidine-2-carboxylic acid amide which exhibit good inhibitory effect upon the interaction of CAMs and Leukointegrins and are thus useful in the treatment of inflammatory disease.

8 Claims, No Drawings

DERIVATIVES OF [6,7-DIHYDRO-5H-IMIDAZO[1,2-A]IMIDAZOLE-3-SULFONYL]-PYRROLIDINE-2-CARBOXYLIC ACID AMIDE

CROSS REFERENCE TO RELATED APPLICATIONS

This application is a divisional of U.S. application Ser. No. 10/685,638, filed Oct. 15, 2003, which application claims the benefit of U.S. Provisional Application No. 60/422,449, filed on Oct. 30, 2002, which applications are both herein incorporated by reference in their entirety.

BACKGROUND OF THE INVENTION

1. Technical Field

The present invention relates generally to a series of novel derivatives of [6,7-dihydro-5H-imidazo[1,2-a]imidazole-3-sulfonyl]-pyrrolidine-2-carboxylic acid amide, the synthesis of these compounds and their use in the treatment of inflammatory disease.

2. Background Information

Research spanning the last decade has helped to elucidate the molecular events attending cell-cell interactions in the body, especially those events involved in the movement and activation of cells in the immune system. See generally, Springer, T. *Nature,* 1990, 346, 425-434. Cell surface proteins, and especially the Cellular Adhesion Molecules ("CAMs") and "Leukointegrins", including LFA-1, MAC-1 and gp150.95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117-138 and Diamond, M.; Springer, T. *Current Biology,* 1994, 4, 506-532.

A group of individuals has been identified which lack the appropriate expression of Leukointegrins, a condition termed "Leukocyte Adhesion Deficiency" (Anderson, D. C.; et al., *Fed. Proc.* 1985, 44, 2671-2677 and Anderson, D. C.; et al., *J. Infect. Dis.* 1985, 152, 668-689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD 18 family. By virtue of the fact that LAD patients who lack CD 18 cannot mount an inflammatory response, it is believed that antagonism of CD18, CD11/ICAM interactions will also inhibit an inflammatory response.

It has been demonstrated that the antagonism of the interaction between the CAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; *Immunology Today,* 1994, 15, 251-255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: *Adhesion Molecules*; Wegner, C. D., Ed.; 1994, 1-38, Cosimi, C. B.; et al., *J. Immunol.* 1990, 144, 4604-4612 and Kavanaugh, A.; et al., *Arthritis Rheum.* 1994, 37, 992-1004) and antibodies directed against LFA-1 have demonstrated immunosuppressive effects in bone marrow transplantation and in the prevention of early rejection of renal allografts (Fischer, A.; et al., *Lancet,* 1989, 2, 1058-1060 and Le Mauff, B.; et al., *Transplantation,* 1991, 52, 291-295).

It has also been demonstrated that a recombinant soluble form of ICAM-1 can act as an inhibitor of the ICAM-1 interaction with LFA-1. Soluble ICAM-1 acts as a direct antagonist of CD18,CD11/ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al, *J. Immunol.* 1993, 151, 7224 and Roep, B. O.; et al., *Lancet,* 1994, 343, 1590).

Thus, the prior art has demonstrated that large protein molecules which antagonize the binding of the CAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

It follows that small molecules having the similar ability as large protein molecules to directly and selectively antagonize the binding of the CAMs to the Leukointegrins would make preferable therapeutic agents.

Several small molecules have been described in the literature that affect the interaction of CAMs and Leukointegrins. For example, U.S. Pat. No. 6,355,664 and the corresponding WO 98/39303 disclose a class of small molecule, having a hydantoin core, that are inhibitors of the interaction of LFA-1 and ICAM-1. WO 01/07440 A1 discloses compounds having this same activity that instead have a 6,7-dihydro-5H-imidazo [1,2-a]imidazole-3-sulfonyl core. While the compounds that are described by WO 01/07440 A1 have a more potent inhibitory affect upon the interaction of CAMs and Leukointegrins than do the hydantoins of U.S. Pat. No. 6,355,664 and the corresponding WO9839303, they nevertheless are not ideal therapeutic agents because the rate at which they are metabolized is undesirably high.

Thus, the problem to be solved by the present invention is to find small molecules that have not only good inhibitory effect upon the interaction of CAMs and Leukointegrins but that also are metabolized at a rate that is not overly rapid.

BRIEF SUMMARY OF THE INVENTION

The invention comprises a class of derivatives of [6,7-dihydro-5H-imidazo[1,2-a]imidazole-3-sulfonyl]-pyrrolidine-2-carboxylic acid amide and methods for making the same. These compounds are useful for the treatment of inflammatory conditions in that they exhibit good inhibitory effect upon the interaction of CAMs and Leukointegrins and are metabolized fairly slowly. Thus, the invention further comprises the use of these compounds for the treatment of inflammatory conditions and pharmaceutical compositions comprising the same as active ingredients.

DETAILED DESCRIPTION OF THE INVENTION

In its broadest generic aspect, the invention comprises compounds of the formula I

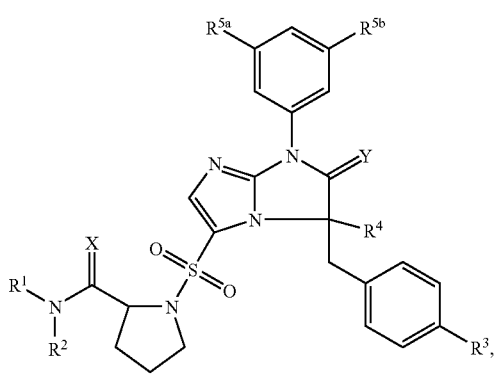

wherein:
$R^1$ and $R^2$ are each, independently selected from the group consisting of:
(A) hydrogen, with the proviso that $R^1$ and $R^2$ are not both hydrogen atoms;
(B) —$R^{100}$, which is:
a straight or branched alkyl of 1 to 7 carbon atoms or cycloalkyl of 3 to 6 carbon atoms, which alkyl or cycloalkyl group is mono- or poly substituted with moieties independently selected from the group consisting of:
(i) oxo,
(ii) cyano,
(iii) halogen,
(iv) moieties of the formula —$COOR^6$, wherein $R^6$ is a hydrogen atom, a straight or branched alkyl of 1 to 7 carbon atoms or cycloalkyl of 3 to 6 carbon atoms,
(v) moieties of the formula —$OR^7$, wherein $R^7$ is a hydrogen atom, a straight or branched alkyl group of 1 to 7 carbon atoms or an acyl group of the formula —$COR^8$ wherein $R^8$ is a straight or branched alkyl group of 1 to 7 carbon atoms,
(vi) moieties of the formula —$NR^9R^{10}$, wherein $R^9$ and $R^{10}$ are each, independently selected from the group consisting of:
(a) hydrogen,
(b) straight or branched alkyl of 1 to 7 carbon atoms,
(c) acyl of the formula —$COR^{11}$ wherein $R^{11}$ is a straight or branched alkyl group of 1 to 7 carbon atoms, and
(d) groups of the formula —$COOR^{12}$ wherein $R^{12}$ is a straight or branched alkyl group of 1 to 7 carbon atoms,
or wherein $R^9$ and $R^{10}$ constitute a bridge consisting of 3-5 methylene groups or 2-4 methylene groups and one oxygen atom, such that the groups $R^9$ and $R^{10}$ together with the nitrogen atom between them form a heterocyclic ring,
(vii) saturated, heterocyclic groups, consisting of 3 to 5 methylene groups and one oxygen atom, wherein said heterocyclic groups are optionally mono- or disubstituted with moieties that are independently selected from the group consisting of:
(a) oxo and
(b) straight or branched alkyl of 1 to 3 carbon atoms; and
(viii) aryl, selected from the class consisting of:
(a) furyl,
(b) tetrazolyl and
(c) thiophenyl;
(C) aryl, selected from the group consisting of:
(i) biphenyl,
(ii) phenyl which is mono- or di-substituted with moieties independently selected from the group consisting of —$NH_2$ and N-morpholino, and
(iii) quinolinyl; and
(D) unsaturated or partially saturated heterocyclic groups consisting of 2 to 3 carbon atoms, 1 to 2 nitrogen atoms, 0 to 1 sulfur atoms and 0 to 1 oxygen atoms wherein said heterocyclic group is optionally mono- or polysubstituted with one or more of the following moieties independently selected from the group consisting of:
(i) oxo and
(ii) straight or branched alkyl of 1 to 7 carbon atoms;
or wherein $R^1$ and $R^2$ constitute a saturated 3 to 5 methylene group bridge which together with the nitrogen atom between them form a heterocyclic ring, wherein said heterocyclic ring is mono- or disubstituted with moieties independently selected from the group consisting of:
(A) —OH,
(B) —COOH and
(C) —$CONH_2$;
$R^3$ is:
(A) aryl selected from the group consisting of pyridyl and pyrimidyl, wherein one or more hydrogen atoms of said aryl group are optionally and independently substituted with moieties selected from the group consisting of:
(i) cyano,
(ii) halogen and
(iii) groups of the formula —$NR^{13}R^{14}$, wherein $R^{13}$ and $R^{14}$ are each, independently, hydrogen or straight or branched alkyl of 1 to 3 carbon atoms;
(B) trifluoromethoxy or,
(C) cyano;
$R^4$ is straight or branched alkyl of 1 to 3 carbon atoms;
$R^{5a}$ is $C_1$ or $CF_3$;
$R^{5b}$ is $C_1$ or $CF_3$;
X is an oxygen or a sulfur atom; and
Y is an oxygen or a sulfur atom.

In a preferred generic aspect, the invention comprises compounds of the formula I, wherein:

$R^1$ and $R^2$ are each independently selected from the group consisting of:
  (A) hydrogen with the proviso that $R^1$ and $R^2$ are not both hydrogen atoms;
  (B) —$R^{100}$, which is:
    a straight or branched alkyl of 1 to 4 carbon atoms, which alkyl group is mono- or disubstituted with moieties independently selected from the group consisting of:
      (i) oxo,
      (ii) OH,
      (iii) moieties of the formula —$NR^9R^{10}$, wherein $R^9$ and $R^{10}$ are each, independently selected from a group consisting of:
        (a) hydrogen and
        (b) methyl,
      (iv) tetrazole,
    or wherein $R^1$ and $R^2$ constitute a saturated 5 methylene group bridge which together with the nitrogen atom between them form a heterocyclic ring, wherein said heterocyclic ring is monosubstituted with COOH;

$R^3$ is:
  (A) aryl selected from the group consisting of 3-pyridyl and 5-pyrimidyl wherein said aryl group is monosubstituted with:
    (i) cyano or
    (ii) $NH_2$,
  (B) trifluoromethoxy or
  (C) cyano;

$R^4$ is a methyl group;
$R^{5a}$ is Cl;
$R^{5b}$ is Cl;
X is an oxygen atom and
Y is an oxygen atom.

In a penultimately preferred generic aspect, the invention comprises compounds of the formula I wherein:

$R^1$ and $R^2$ are each, independently selected from the group consisting of:
  (A) hydrogen with the proviso that $R^1$ and $R^2$ are not both hydrogen atoms, or
  (B) —$R^{100}$, which is:
    straight or branched alkyl of 1 to 4 carbon atoms, which alkyl group is mono- or disubstituted with moieties independently selected from the group consisting of:
      (i) oxo,
      (ii) OH and
      (iii) $NH_2$;

$R^3$ is trifluoromethoxy or cyano;
$R^4$ is a methyl group;
$R^{5a}$ is Cl;
$R^{5b}$ is Cl;
X is an oxygen atom; and
Y is an oxygen atom.

It will be appreciated that the compounds of the formula I have at least two chiral centers. In an ultimately preferred generic aspect, the invention includes compounds of formula I with the absolute stereochemistry depicted below in formula I*.

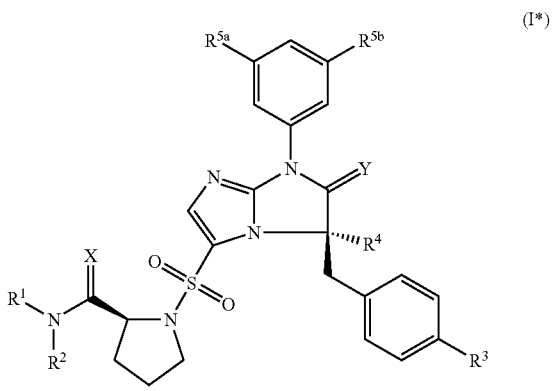

Specifically preferred compounds of formula I of the invention are those selected from the group consisting of:
({(S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carbonyl}-amino)-acetic acid, ({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-acetic acid, (S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (2-hydroxy-2-methyl-propyl)-amide, (S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (2-hydroxy-ethyl)-amide, (S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid carbamoylmethyl-amide, (S)-1-[(R)-5-[4-(2-Cyano-pyridin-3-yl)-benzyl]-7-(3,5-dichloro-phenyl)-5-methyl-6-oxo-6,7-dihydro-5H-imidazo[1,2-a]imidazole-3-sulfonyl]-pyrrolidine-2-carboxylic acid (2-hydroxy-2-methyl-propyl)-amide, (S)-1-[(R)-5-[4-(2-Cyano-pyridin-3-yl)-benzyl]-7-(3,5-dichloro-phenyl)-5-methyl-6-oxo-6,7-dihydro-5H-imidazo[1,2-a]imidazole-3-sulfonyl]-pyrrolidine-2-carboxylic acid carbamoylmethyl-amide, (S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (1H-tetrazol-5-ylmethyl)-amide, (S)-1-[(R)-7-(3,5-Dichloro-phenyl)-5-methyl-6-oxo-5-(4-trifluoromethoxy-benzyl)-6,7-dihydro-5H-imidazo[1,2-a]imidazole-3-sulfonyl]-pyrrolidine-2-carboxylic acid (2-hydroxy-2-methyl-propyl)-amide, and (S)-1-[(R)-7-(3,5-Dichloro-phenyl)-5-methyl-6-oxo-5-(4-trifluoromethoxy-benzyl)-6,7-dihydro-5H-imidazo[1,2-a]imidazole-3-sulfonyl]-pyrrolidine-2-carboxylic acid carbamoylmethyl-amide.

The invention also includes pharmaceutically acceptable salts of the compounds of the formula I.

General Synthetic Methods

Compounds of the invention may be prepared by the general methods described below. Typically, reaction progress may be monitored by thin layer chromatography (TLC) if desired. If desired, intermediates and products may be purified by chromatography on silica gel and/or recrystallization, and characterized by one or more of the following techniques: NMR, mass spectroscopy and melting point. Starting materials and reagents are either commercially available or may be prepared by one skilled in the art using methods described in the chemical literature.

Compounds of formula I may be prepared from intermediate II. The synthesis of intermediate II is reported by Wu et al., U.S. Non-provisional application Ser. No. 09/604,312 and Frutos et al., U.S. Pat. No. 6,441,183, both incorporated herein by reference.

Intermediate II may be prepared by the procedure illustrated in Scheme I.

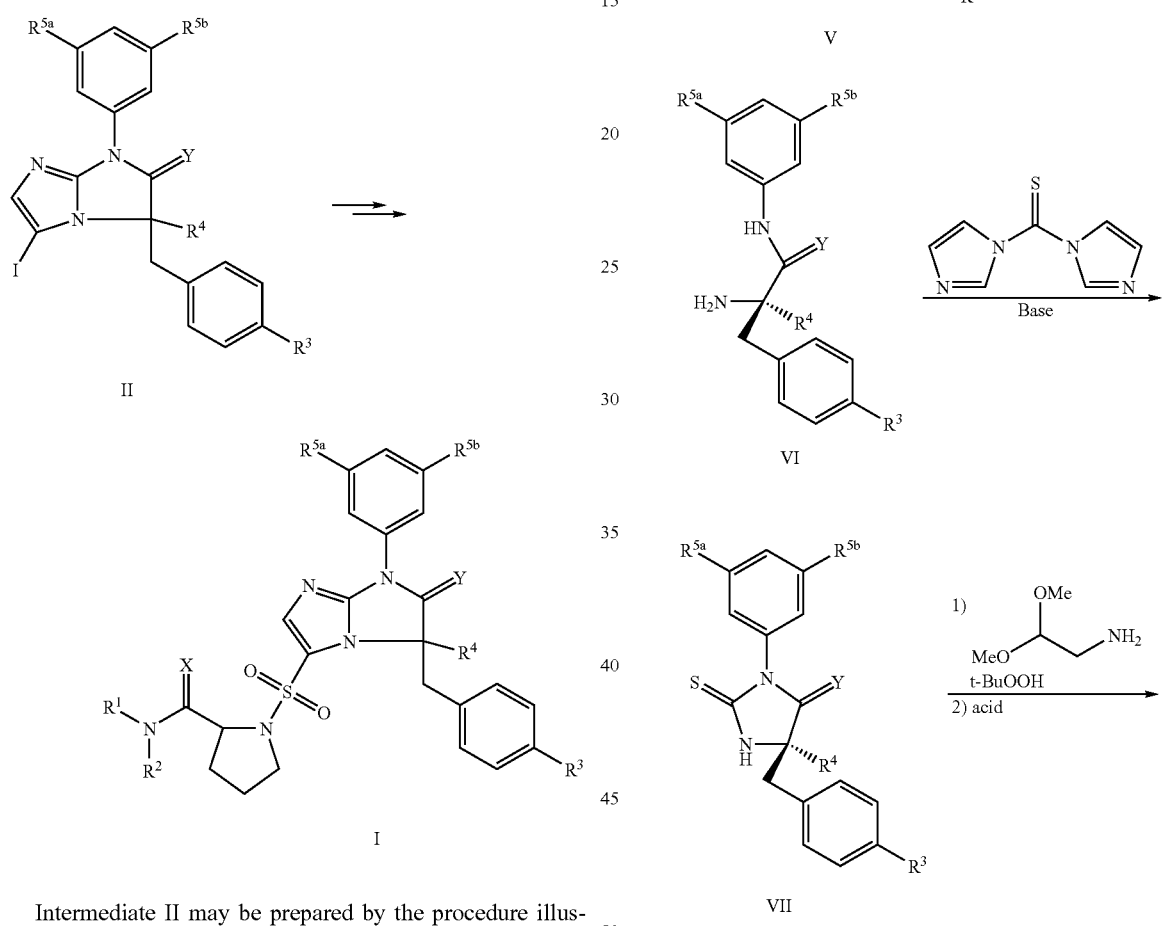

-continued

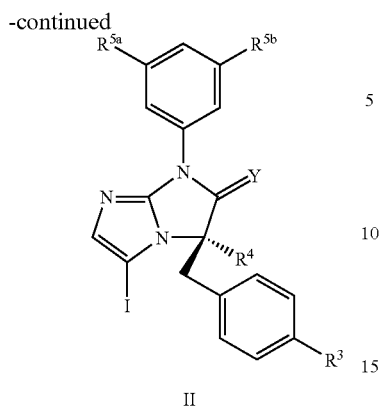

II

As illustrated above, intermediate III is deprotonated with a suitable base such as lithium bis(trimethylsilyl)amide at about −20° C. to −30° C., and then alkylated with a substituted benzyl halide, preferably a benzyl bromide (IV) to produce V. Hydrolysis of the trifluoroacetamide group of V, for example by treatment with 40% aqueous benzyltrimethylammonium hydroxide in dioxane/50% NaOH, followed by treatment with acid, such as HCl, provides VI. Treatment of VI with thiocarbonyldiimidazole in the presence of a base such as 4-(N,N-dimethylamino)pyridine (DMAP) provides VII. Treatment of VII with aminoacetaldehyde dimethyacetal and t-butylhydroperoxide solution, followed by treatment of the intermediate acetal with an acid such as p-toluenesulfonic acid provides VIII. Iodination of VIII by treatment with an iodinating agent such as N-iodosuccinamide provides II.

The method used for preparation of intermediate III, treatment of the amide formed from N-Boc-D-alanine and 3,5-dichloroaniline with trifluoroacetic acid to remove the Boc-group, followed by treatment with pivalaldehyde, and acylation of the resulting imidazolodone with trifluoroacetic anhydride is described in U.S. Pat. No. 6,414,161, cited above, and in the chemical literature (N. Yee, Org Lett., 2000, 2, 2781).

The synthesis of compounds of formula I from intermediate II is illustrated in Scheme II.

Scheme II

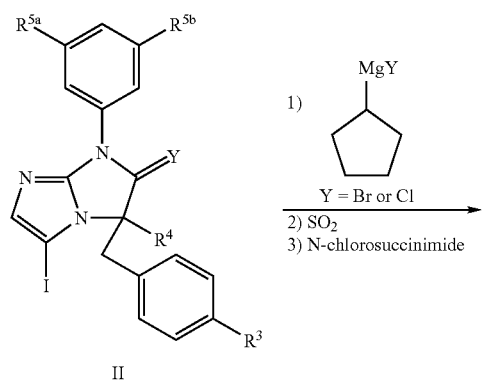

-continued

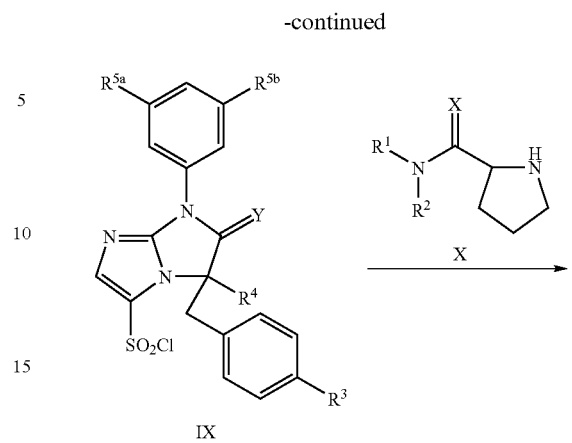

IX

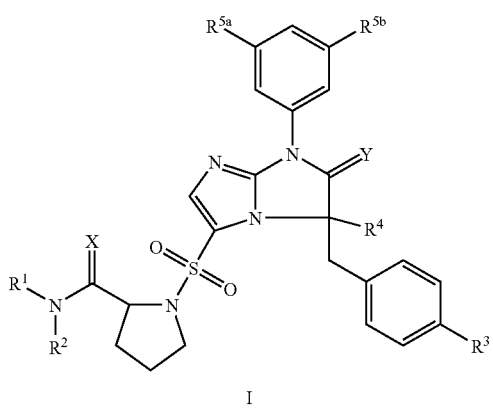

I

As illustrated above, treatment of II with a Grignard reagent, such as cyclopentyl magnesium bromide or chloride, followed by treatment of the resulting magnesium salt with SO$_2$ and then N-chlorosuccinimide provides the sulfonyl chloride IX. Treatment of 1x with the desired amine (X) in the presence of a suitable base such as triethylamine, provides the desired product of formula (I). Intermediates X are either commercially available or readily prepared from commercially available starting materials by methods known in the art. The initial product of formula I may be further modified by methods known in the art to provide additional compounds of the invention. Several examples are provided in the Synthetic Examples section.

The desired R$^3$ on formula I compounds may be obtained by selection of the appropriately substituted intermediate IV in Scheme I. Alternately, intermediate VIII having R$^3$ being Br (VIIIa) may be converted to intermediates having R$^3$ being CN or an optionally substituted 5-pyrimidyl group as illustrated in Scheme III.

Scheme III

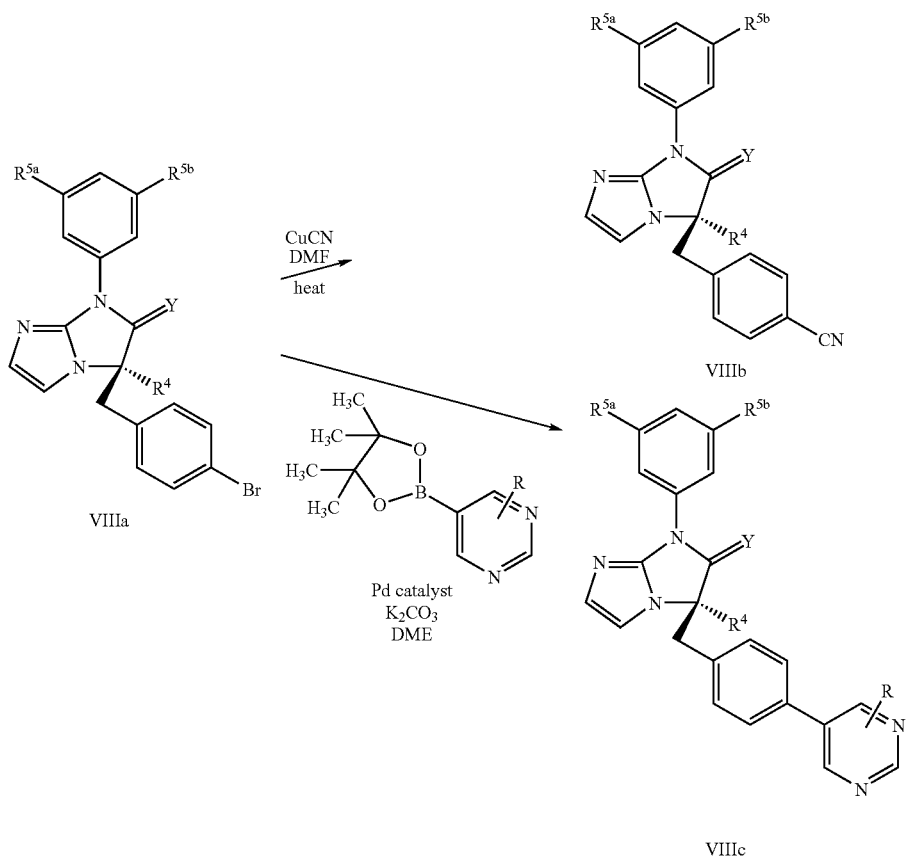

As illustrated above, the aryl bromide VIIIa is treated with a cyanide salt, preferably CuCN and heated in a suitable solvent such as DMF to provide the cyano-intermediate VIIb. Treatment of VIIIa with a pyrimidine boronate ester such as 5-(4,4,5,5,-tetramethyl-[1,3,2]dioxaborolan-2-yl)-pyrimidine in the presence of a palladium catalyst such as [1,1'-bis(diphenylphosphino)ferrocene]dichloropalladium(II). $CH_2Cl_2$ ($PdCl_2$(dppf).$CH_2Cl_2$) and a base such as potassium carbonate in a suitable solvent (Suzuki reaction), for example dimethoxyethane, provides the pyrimidine intermediate VIIc. Intermediates VIIb and VIIc may then be converted to desired compounds of formula I by the procedures described in Schemes I and II. The Suzuki reaction to convert $R_3$=Br to $R_3$=an optionally substituted pyrimidine may also be carried out on a compound of formula I.

The invention is further described by the following synthetic examples.

SYNTHETIC EXAMPLES

Example 1

Synthesis of (R)-1-(3,5-dichloro-phenyl)-3-methyl-3-(4-trifluoromethoxy-benzyl)-1H-imidazo[1,2-a]imidazol-2-one

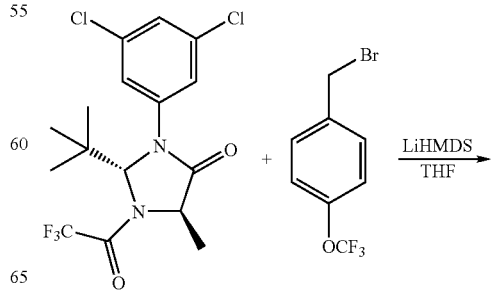

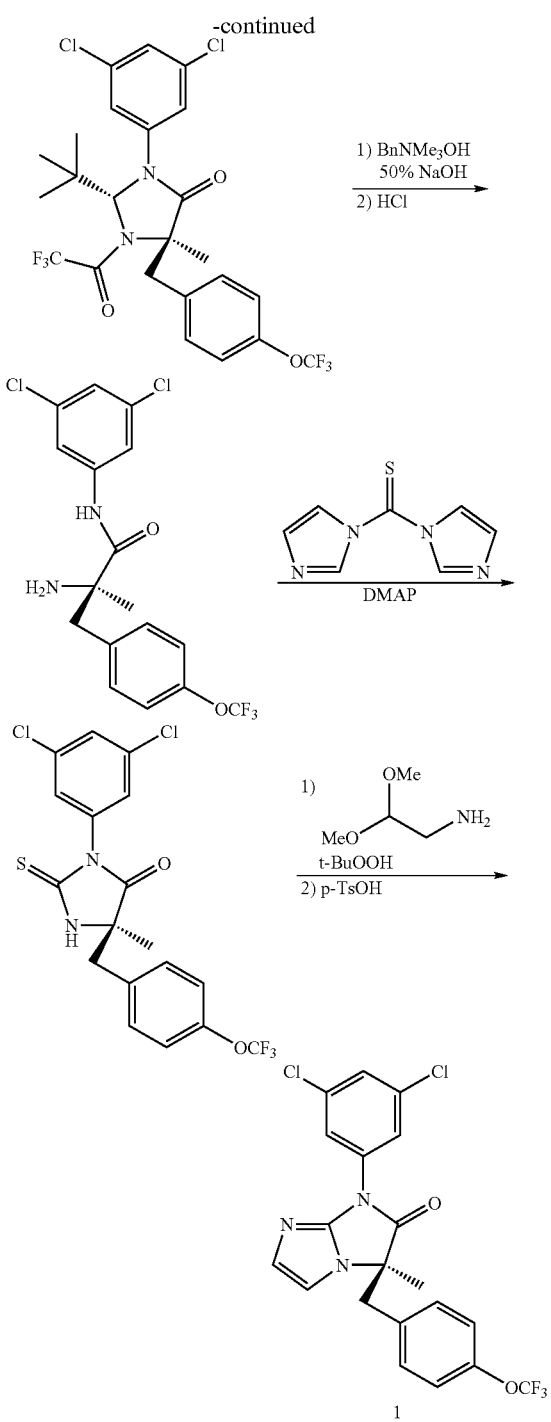

Lithium bis(trimethylsilyl)amide (LiHMDS) (38.0 mL, 1 M in THF) was added slowly dropwise over 25 min to a solution of (2S,5R)-2-tert-butyl-3-(3,5-dichloro-phenyl)-5-methyl-1-(2,2,2-trifluoro-acetyl)-imidazolidin-4-one (10.0 g, 25.17 mmol) in 60 mL of THF at −20° C. After stirring at −20° C. for 20 min, a solution of 4-trifluoromethoxybenzyl bromide (6.04 mL, 37.76 mmol) in 30 mL of THF was added dropwise over 20 min. The mixture was stirred at −20° C. for 45 min, warmed to −5° C. over 1 h, and then poured over 50 mL of ice-cold saturated NH₄Cl solution. The resulting mixture was extracted with two portions of EtOAc (200, 100 mL).

The combined organic phases were washed with brine, dried over Na₂SO₄, filtered and concentrated. The crude product was triturated with hexanes to afford 12.5 g (87%) of (2R, 5R)-2-tert-butyl-3-(3,5-dichloro-phenyl)-5-methyl-1-(2,2,2-trifluoro-acetyl)-5-(4-trifluoromethoxy-benzyl)-imidazolidin-4-one as an off-white solid.

To a solution of the above imidazolidinone (6.0 g, 10.5 mmol) in 40 mL of dioxane was added 40% aqueous benzyltrimethylammonium hydroxide (6.59 g, 15.75 mmol) at room temperature. As the mixture was warmed to 40° C., 50% aqueous sodium hydroxide (1.68 g, 21.0 mmol) was added slowly dropwise over 5 min. The mixture was stirred at 40° C. for 18 h, then a solution of 6.4 g of conc HCl in 3.3 mL of water was added slowly dropwise over 10 min. The mixture was warmed to 50° C. and stirred for an additional 5 h, then cooled to room temperature and concentrated. 50 mL of toluene was added to the residue, and the biphasic mixture was stirred vigorously as 50% aqueous sodium hydroxide (3.0 g) was added slowly dropwise (pH of the aqueous phase ≧10). The aqueous layer was extracted with two portions of toluene, and the combined organic phases were washed with water and brine, dried over Na₂SO₄, filtered and concentrated to afford 4.24 g of (R)-2-amino-N-(3,5-dichloro-phenyl)-2-methyl-3-(4-trifluoromethoxy-phenyl)-propionamide as a light brown oil.

To a solution of the above propionamide (4.24 g, 10.41 mmol) in 30 mL of THF was added thiocarbonyldiimidazole (2.81 g, 15.77 mmol) and DMAP (0.127 g, 1.04 mmol). The mixture was heated at reflux for 17 h, cooled to room temperature, and concentrated. The orange oily residue was dissolved in 50 mL of toluene and treated slowly dropwise with 20 mL of 5% aqueous HCl solution. After stirring the mixture for 10 min, the aqueous layer was separated and extracted with 30 mL of toluene. The combined organic phases were washed with four 20-mL portions of water and 20 mL of brine, dried over Na₂SO₄, filtered and concentrated to provide 4.48 g of (R)-3-(3,5-dichloro-phenyl)-5-methyl-2-thioxo-5-(4-trifluoromethoxy-benzyl)-imidazolidin-4-one as an orange foam.

To a solution of the above thiohydantoin (4.47 g, 9.95 mmol) and aminoacetaldehyde dimethylacetal (6.50 mL, 59.7 mmol) in 20 mL of MeOH was added 7.69 mL (59.7 mmol, 70% in water) of t-butyl hydroperoxide solution, dropwise over 25 min. During the addition and for about 1 h after, the internal temperature of the mixture was kept below 20° C. with an ice water bath. The mixture was stirred at room temperature for 86 h, and 25 mL of saturated NaHSO₃ solution was added slowly dropwise, maintaining the internal temperature below 20° C. with an ice water bath. The resulting cloudy white mixture was concentrated. To the residue was added EtOAc, and this mixture was concentrated again. The oily residue was partitioned between 30 mL of EtOAc and 20 mL of water, and the aqueous phase was separated and extracted with 20 mL of EtOAc. The combined organic layers were washed with 25 mL of water and brine, dried over Na₂SO₄, filtered and concentrated to give 5.21 g of (R)-3-(3, 5-dichloro-phenyl)-2-[(E)-2,2-dimethoxy-ethylimino]-5-methyl-5-(4-trifluoromethoxy-benzyl)-imidazolidin-4-one as a thick yellow oil.

A solution of the above crude acetal (5.20 g, 9.95 mmol) in 30 mL of acetone was treated with p-toluenesulfonic acid (1.89 g, 9.96 mmol). The mixture was heated at reflux for 2 h, then cooled to room temperature and concentrated. The resulting dark orange oil was dissolved in 40 mL of EtOAc and treated carefully with a solution of 2.3 g of NaHCO₃ in 23 mL of water. After gas evolution ceased, the aqueous phase was separated and extracted with two portions of EtOAc. The combined organic layers were washed with saturated NaHCO$_3$ solution, two portions of water, and brine, dried over Na$_2$SO$_4$, filtered and concentrated. The oily residue was purified by silica gel chromatography to afford 1.58 g of the title compound as a thick colorless oil (456.2, M+1).

Example 2

Synthesis of (R)-7-(3,5-dichloro-phenyl)-5-methyl-6-oxo-5-(4-trifluoromethoxy-benzyl)-6,7-dihydro-5H-imidazo[1,2-a]imidazole-3-sulfonyl chloride

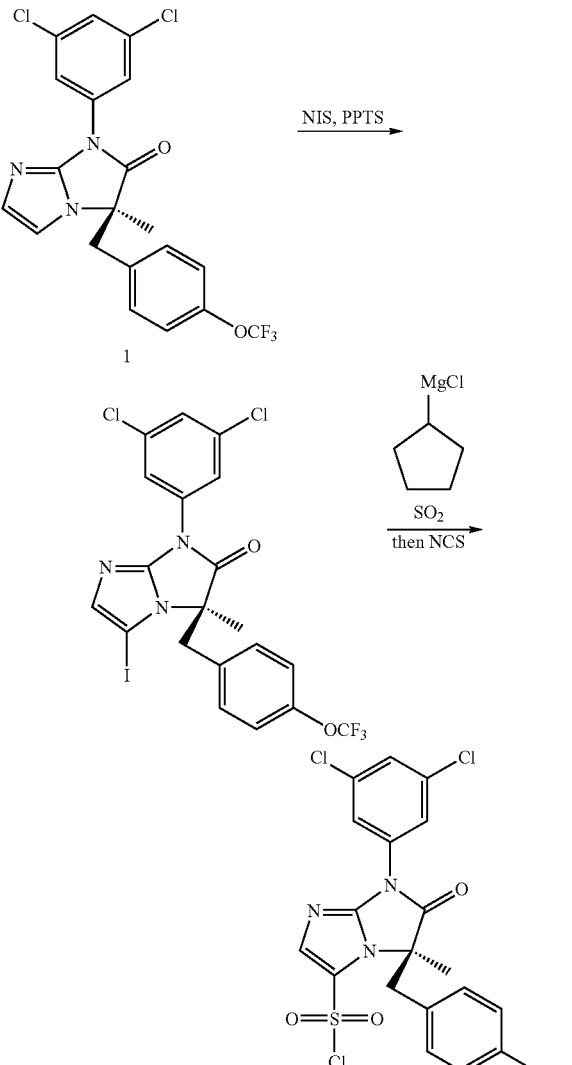

A solution of (R)-1-(3,5-dichloro-phenyl)-3-methyl-3-(4-trifluoromethoxy-benzyl)-1H-imidazo[1,2-a]imidazol-2-one (Example 1) (1.54 g, 3.38 mmol) in 30 mL of THF was treated with N-iodosuccinimide (0.846 g, 3.76 mmol) and pyridinium p-toluenesulfonate (0.086 g, 0.37 mmol). The mixture was stirred at room temperature for 17 h, then diluted with EtOAc and washed with 10% Na$_2$S$_2$O$_3$ solution and water. The combined aqueous layers were extracted with 10 mL of EtOAc. The combined organic phases were washed with 25 mL of brine, dried over Na$_2$SO$_4$, filtered and concentrated. The crude orange oil was purified by silica gel chromatography to provide 1.27 g (65%) of (R)-1-(3,5-dichloro-phenyl)-5-iodo-3-methyl-3-(4-trifluoromethoxy-benzyl)-1H-imidazo[1,2-a]imidazol-2-one as an off-white oil (582.0, M+1).

A solution of the above iodide (1.24 g, 2.13 mmol) in 16 mL of THF was cooled at −40° C. as cyclopentyl magnesium chloride (1.17 mL, 2 M in diethyl ether) was added dropwise over 10 min. After stirring at −40° C. for 1 h, SO$_2$ (g) was added by placing an inlet needle just above the surface of the reaction mixture for 1.5 min. The bright yellow mixture was warmed to −20° C. over 1 h and then stirred at room temperature for 1 h. N$_2$ (g) was bubbled through the mixture for 20 min followed by concentration and pumping under high vacuum for 12 h. The resulting yellow foam was dissolved in 16 mL of THF and cooled at −20° C. as a solution of N-chlorosuccinimide (0.341 g, 2.56 mmol) in 8 mL of THF was added dropwise over 5 min. After stirring at −20° C. for 1 h, the mixture was poured over ice and extracted with two portions of EtOAc. The combined organic layers were washed with 20 mL of ice-cold brine, dried over Na$_2$SO$_4$, filtered and concentrated. Purification by silica gel chromatography provided 0.975 g (83%) of the title compound as a thick oil (554.2, M+1).

Example 3

Synthesis of (S)-1-[(R)-7-(3,5-dichloro-phenyl)-5-methyl-6-oxo-5-(4-trifluoromethoxy-benzyl)-6,7-dihydro-5H-imidazo[1,2-a]imidazole-3-sulfonyl]-pyrrolidine-2-carboxylic acid (2-hydroxy-2-methyl-propyl)-amide

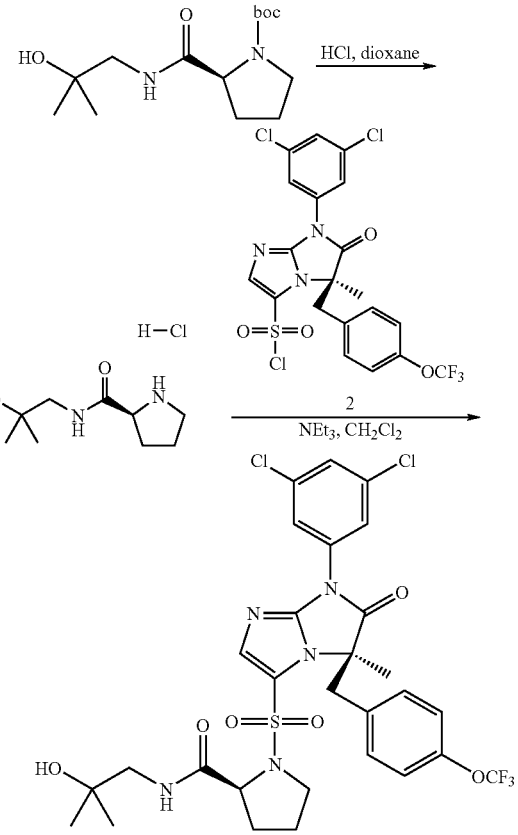

To a suspension of (S)-2-(2-hydroxy-2-methyl-propylcarbamoyl)-pyrrolidine-1-carboxylic acid tert-butyl ester (see Example 11) (0.190 g, 0.663 mmol) in 1 mL of dioxane was added HCl (2.0 mL, 4 M in dioxane), and the resulting cloudy mixture was stirred at room temperature for 4 h. Concentration of the mixture was followed by addition of $CH_2Cl_2$, and this process was repeated twice. Final pumping under high vacuum for 12 h afforded the deprotected amine HCl salt as a pale yellow oil. This crude amine HCl salt was dissolved in 3 mL of $CH_2Cl_2$ and treated with triethylamine (0.200 mL, 1.44 mmol). After stirring at room temperature for 10 min, a solution of (R)-7-(3,5-dichloro-phenyl)-5-methyl-6-oxo-5-(4-trifluoromethoxy-benzyl)-6,7-dihydro-5H-imidazo[1,2-a]imidazole-3-sulfonyl chloride (Example 2) (0.199 g, 0.359 mmol) in 3 mL of $CH_2Cl_2$ was added rapidly dropwise via cannula. The reaction mixture was stirred at room temperature for 3 h, then partitioned between 30 mL of $CH_2Cl_2$ and 10 mL of water. The organic phase was washed with 10 mL of brine, dried over $Na_2SO_4$, filtered and concentrated. The crude product was purified by silica gel chromatography to give 0.228 g (90%) of the title compound as a white foam (704.0, M+1).

Example 4

Synthesis of (S)-1-[(R)-7-(3,5-dichloro-phenyl)-5-methyl-6-oxo-5-(4-trifluoromethoxy-benzyl)-6,7-dihydro-5H-imidazo[1,2-a]imidazole-3-sulfonyl]-pyrrolidine-2-carboxylic acid (2-hydroxy-ethyl)-amide

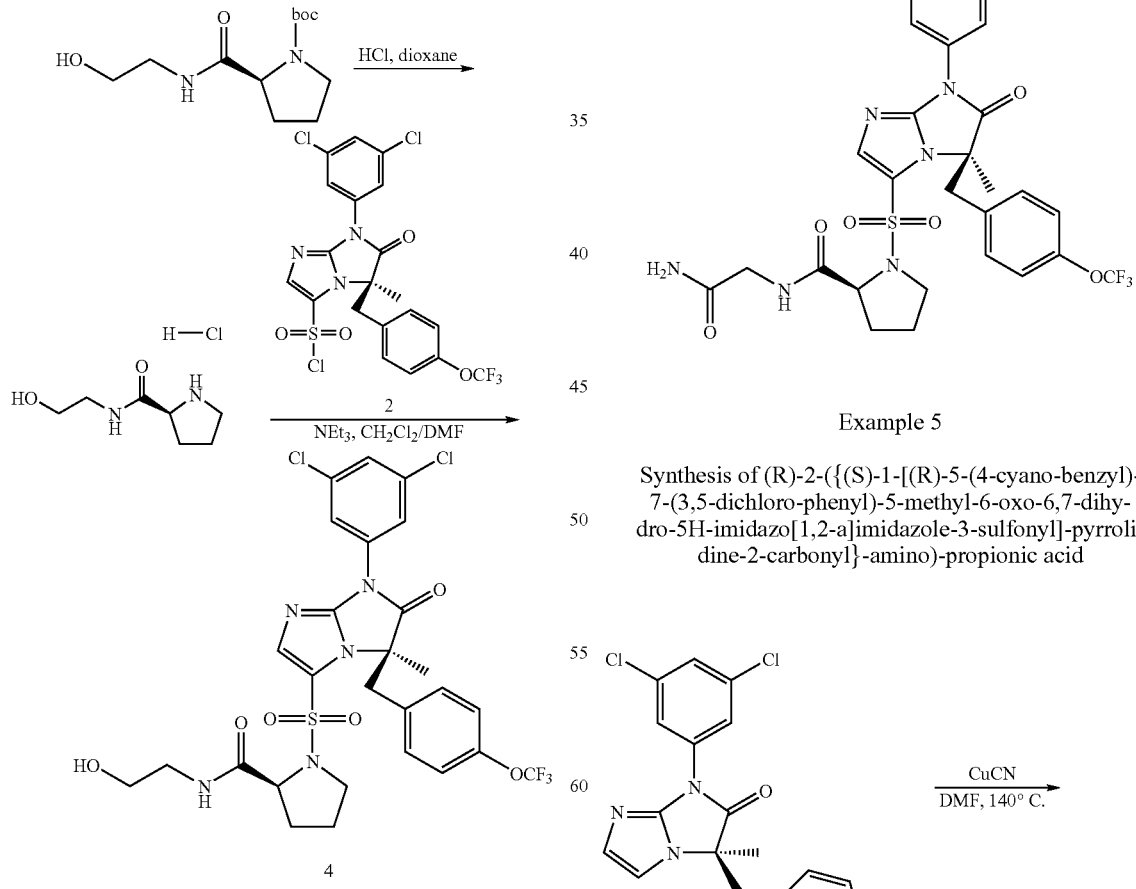

To a suspension of (S)-2-(2-hydroxy-ethylcarbamoyl)-pyrrolidine-1-carboxylic acid tert-butyl ester (0.200 g, 0.774 mmol) in 1 mL of dioxane was added HCl (2.0 mL, 4 M in dioxane), and the resulting cloudy mixture was stirred at room temperature for 4 h. Concentration of the mixture was followed by addition of $CH_2Cl_2$. This process was repeated twice and final pumping under high vacuum for 12 h afforded the deprotected amine HCl salt as a white oil. This crude amine HCl salt was dissolved in 3 mL of DMF and treated with triethylamine (0.212 mL, 1.52 mmol). After stirring at room temperature for 10 min, a solution of (R)-7-(3,5-dichloro-phenyl)-5-methyl-6-oxo-5-(4-trifluoromethoxy-benzyl)-6,7-dihydro-5H-imidazo[1,2-a]imidazole-3-sulfonyl chloride (Example 2) (0.211 g, 0.380 mmol) in 4 mL of $CH_2Cl_2$ was added rapidly dropwise via cannula. The reaction mixture was stirred at room temperature for 2 h. Following the addition of 75 mL of EtOAc, the organic layer was washed with three portions of water, then brine, dried over $Na_2SO_4$, filtered and concentrated. The crude product was purified by preparative TLC to afford 0.218 g (85%) of the title compound as a white foam (676.1, M+1).

The following compound was prepared by a procedure analogous to that described above in Example 4:

(S)-1-[(R)-7-(3,5-Dichloro-phenyl)-5-methyl-6-oxo-5-(4-trifluoromethoxy-benzyl)-6,7-dihydro-5H-imidazo[1,2-a]imidazole-3-sulfonyl]-pyrrolidine-2-carboxylic acid carbamoylmethyl-amide. (689.3, M+1)

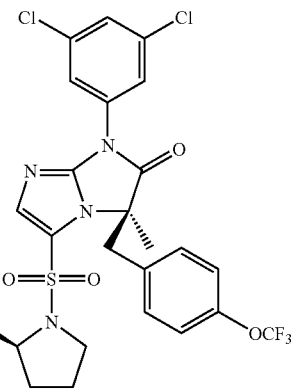

Example 5

Synthesis of (R)-2-({(S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carbonyl}-amino)-propionic acid

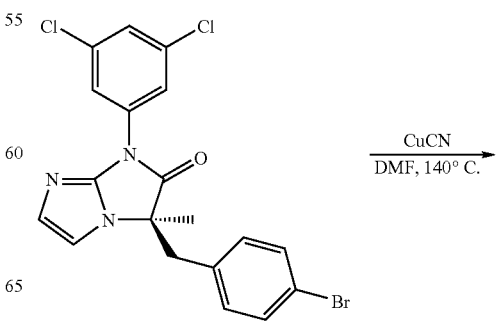

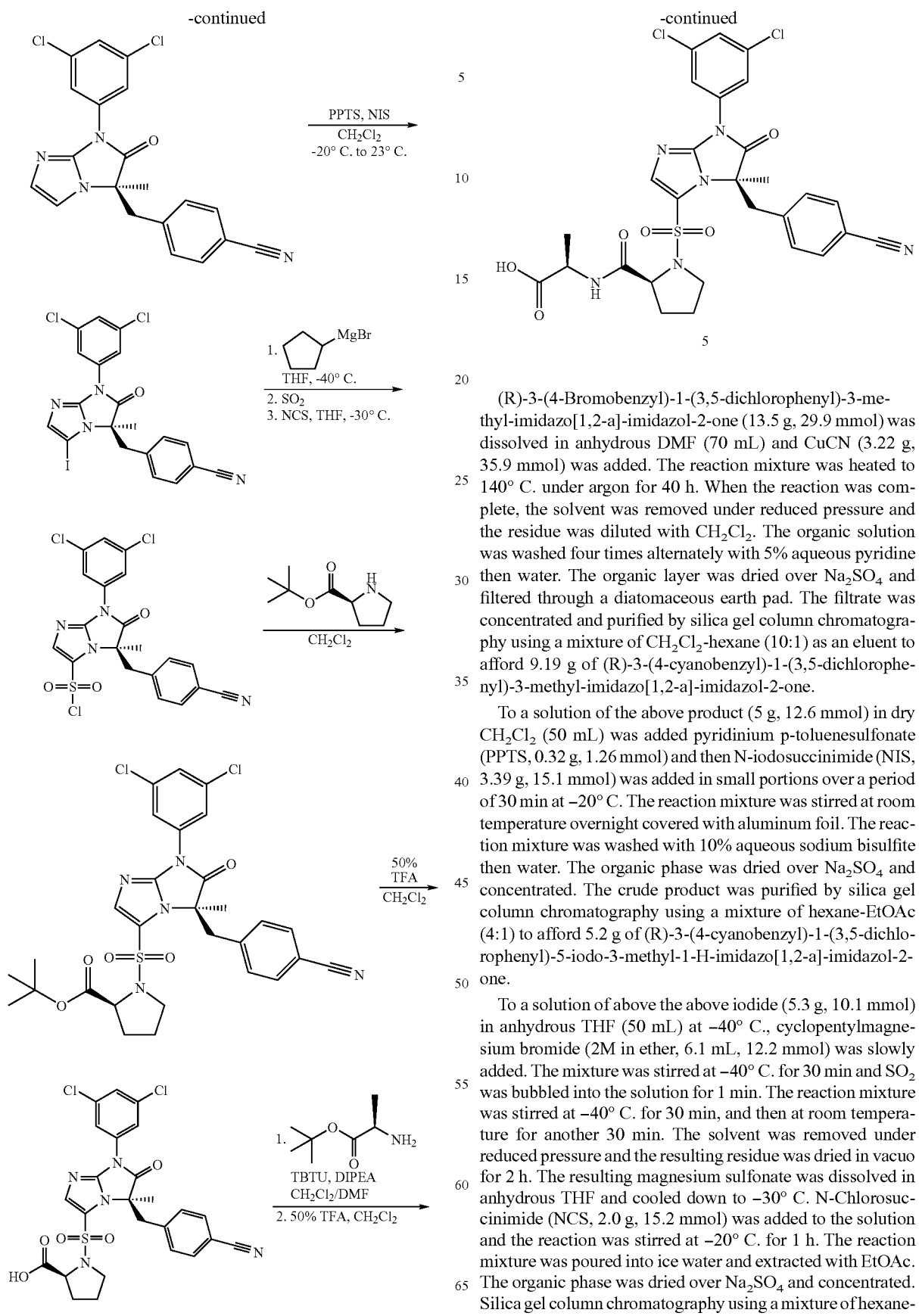

(R)-3-(4-Bromobenzyl)-1-(3,5-dichlorophenyl)-3-methyl-imidazo[1,2-a]-imidazol-2-one (13.5 g, 29.9 mmol) was dissolved in anhydrous DMF (70 mL) and CuCN (3.22 g, 35.9 mmol) was added. The reaction mixture was heated to 140° C. under argon for 40 h. When the reaction was complete, the solvent was removed under reduced pressure and the residue was diluted with $CH_2Cl_2$. The organic solution was washed four times alternately with 5% aqueous pyridine then water. The organic layer was dried over $Na_2SO_4$ and filtered through a diatomaceous earth pad. The filtrate was concentrated and purified by silica gel column chromatography using a mixture of $CH_2Cl_2$-hexane (10:1) as an eluent to afford 9.19 g of (R)-3-(4-cyanobenzyl)-1-(3,5-dichlorophenyl)-3-methyl-imidazo[1,2-a]-imidazol-2-one.

To a solution of the above product (5 g, 12.6 mmol) in dry $CH_2Cl_2$ (50 mL) was added pyridinium p-toluenesulfonate (PPTS, 0.32 g, 1.26 mmol) and then N-iodosuccinimide (NIS, 3.39 g, 15.1 mmol) was added in small portions over a period of 30 min at −20° C. The reaction mixture was stirred at room temperature overnight covered with aluminum foil. The reaction mixture was washed with 10% aqueous sodium bisulfite then water. The organic phase was dried over $Na_2SO_4$ and concentrated. The crude product was purified by silica gel column chromatography using a mixture of hexane-EtOAc (4:1) to afford 5.2 g of (R)-3-(4-cyanobenzyl)-1-(3,5-dichlorophenyl)-5-iodo-3-methyl-1-H-imidazo[1,2-a]-imidazol-2-one.

To a solution of above the above iodide (5.3 g, 10.1 mmol) in anhydrous THF (50 mL) at −40° C., cyclopentylmagnesium bromide (2M in ether, 6.1 mL, 12.2 mmol) was slowly added. The mixture was stirred at −40° C. for 30 min and $SO_2$ was bubbled into the solution for 1 min. The reaction mixture was stirred at −40° C. for 30 min, and then at room temperature for another 30 min. The solvent was removed under reduced pressure and the resulting residue was dried in vacuo for 2 h. The resulting magnesium sulfonate was dissolved in anhydrous THF and cooled down to −30° C. N-Chlorosuccinimide (NCS, 2.0 g, 15.2 mmol) was added to the solution and the reaction was stirred at −20° C. for 1 h. The reaction mixture was poured into ice water and extracted with EtOAc. The organic phase was dried over $Na_2SO_4$ and concentrated. Silica gel column chromatography using a mixture of hexane-EtOAc (5:1) as an eluent afforded 3.0 g of sulfonyl chloride.

The above sulfonyl chloride (1.0 g, 2.02 mmol) was dissolved in CH$_2$Cl$_2$ (10 mL) and L-proline t-butyl ester (1.03 g, 6.06 mmol) was added to the solution. The reaction mixture was stirred at room temperature for 1 h and diluted with CH$_2$Cl$_2$ (5 mL). The organic solution was washed with 1% HCl, saturated NaHCO$_3$ and water. The organic phase was dried over Na$_2$SO$_4$ and concentrated. Silica gel column chromatography using a mixture of hexane-EtOAc (1:1) as an eluent afforded 0.56 g of the desired product. This product was then treated with 50% trifluoroacetic acid (TFA) in CH$_2$Cl$_2$ at room temperature for 2 h. The reaction mixture was diluted with CH$_2$Cl$_2$ and washed with water. The organic layer was dried over Na$_2$SO$_4$ and concentrated to afford 0.45 g of the desired carboxylic acid.

The above carboxylic acid (0.15 g, 0.26 mmol) was dissolved in a mixture of CH$_2$Cl$_2$-DMF (5 mL-0.1 mL). To this solution, were added D-alanine t-butyl ester (0.07 g, 0.39 mmol) and O-benzotriazole-1-yl-N,N,N',N'-tetramethyluronium tetrafluoroborate (TBTU, 0.13 g, 0.39 mmol), followed by N,N-diisopropylethylamine (DIPEA, 0.11 mL, 0.65 mmol). The reaction mixture was stirred at room temperature for 2 h and diluted with CH$_2$Cl$_2$. The solution was washed with 1N HCl and saturated NaHCO$_3$. The organic phase was then dried over Na$_2$SO$_4$ and concentrated. The crude product was purified by preparative thin layer chromatography using EtOAc as an eluent to afford the desired product. The resulting compound was then treated with 50% TFA in CH$_2$Cl$_2$ at room temperature for 2 h. The reaction mixture was diluted with CH$_2$Cl$_2$ and washed with water. The organic layer was dried over Na$_2$SO$_4$ and concentrated. The resulting compound was purified by preparative thin layer chromatography using CH$_2$Cl$_2$-MeOH (95:5) as an eluent to afford 0.119 g of the title compound as a white foam (M+1, 645.2).

The following compound was made by procedures analogous to those described in the above example:

(S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carbonyl}-amino)-acetic acid (631.2, M+1):

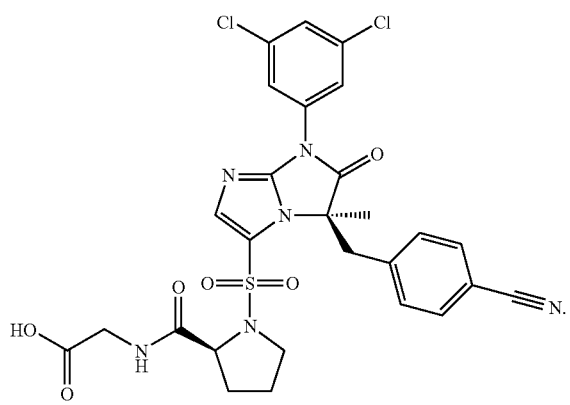

Example 6

Synthesis of 1-{(S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carbonyl}-piperidine-4-carboxylic acid

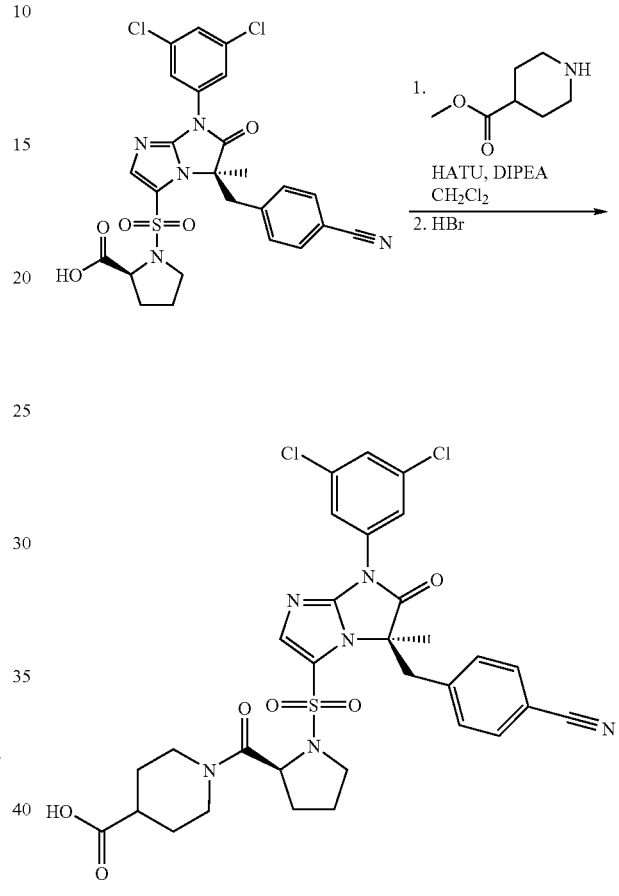

To a stirred solution of (S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (see Example 5) (1 eq) in anhydrous CH$_2$Cl$_2$ and O-(7-azabenzotriazol-1-yl)-N,N,N',N'-tetramethyluronium hexafluorophosphate (HATU) (1.5 eq) was added DIPEA (3 eq) and the mixture was stirred at room temperature for 10 min under nitrogen. Methylisonipecotate (1.5 eq) was added to the reaction mixture and stirred for 2 h at room temperature under nitrogen. The material was purified by column chromatography over silica gel (gradient 10-25% EtOAc in hexane) to provide the methyl ester. The resulting ester (0.140 g, 0.2 mmol) was dissolved in hydrobromic acid in acetic acid (1.0 M) and the reaction was stirred for 4 h. The mixture was concentrated, toluene was added, and the mixture was concentrated again. The resulting residue was chromatographed over silica gel (10% MeOH in methylene chloride) to provide 12 mg of the title compound as a white solid (M+1, 685).

Example 7

(S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid ((S)-2-hydroxy-propyl)-amide

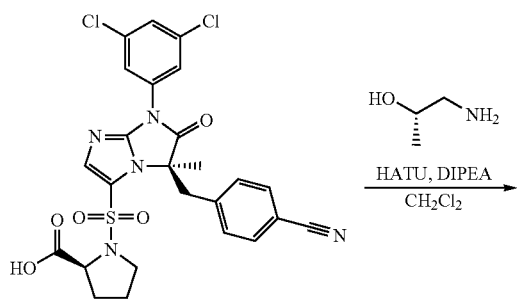

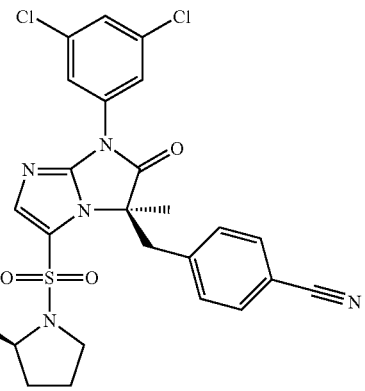

(M+1, 645.1);

(S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (furan-2-ylmethyl)-amide:

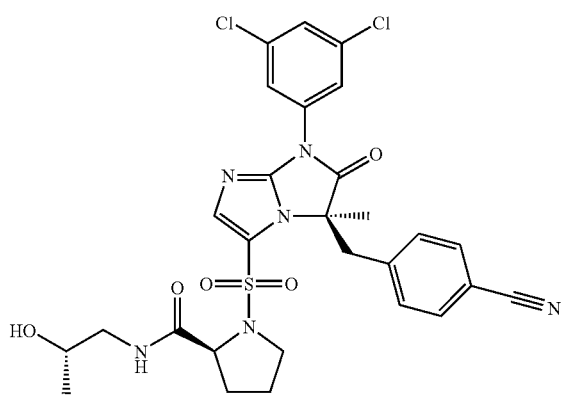

7

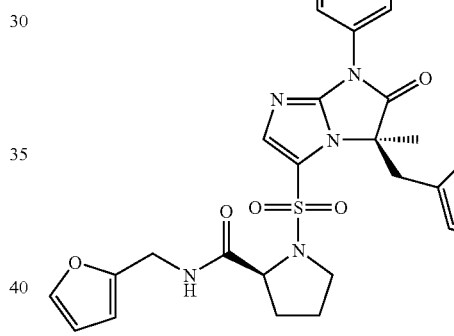

(M+1, 653.2);

Example 8

Synthesis of (S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (4-hydroxy-phenyl)-amide

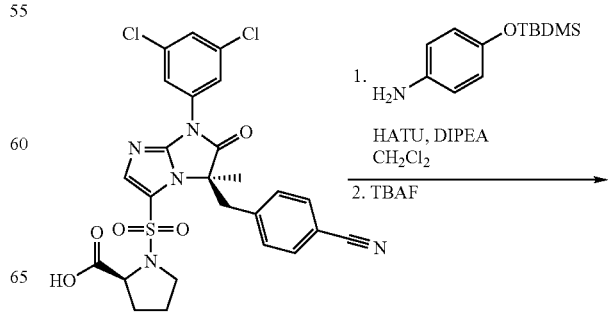

To a stirred solution of (S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (see Example 5) (82 mg, 0.14 mmol) in anhydrous methylene chloride (1 mL) and HATU (82 mg, 0.21 mmol) was added DIPEA (73 µL, 0.42 mmol) and the mixture was stirred for 10 min at room temperature under nitrogen. (S)-1-Aminopropan-2-ol (0.21 mmol) was added and the mixture was stirred for 2 h at room temperature under nitrogen. The material was purified by column chromatography over silica gel to provide 62 mg of the title compound as a white solid (M+1, 631.2).

The following compounds were made by procedures analogous to those described in the above example:

(S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (2-hydroxy-1,1-dimethyl-ethyl)-amide:

Example 9

Synthesis of (S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid acetyl-amide

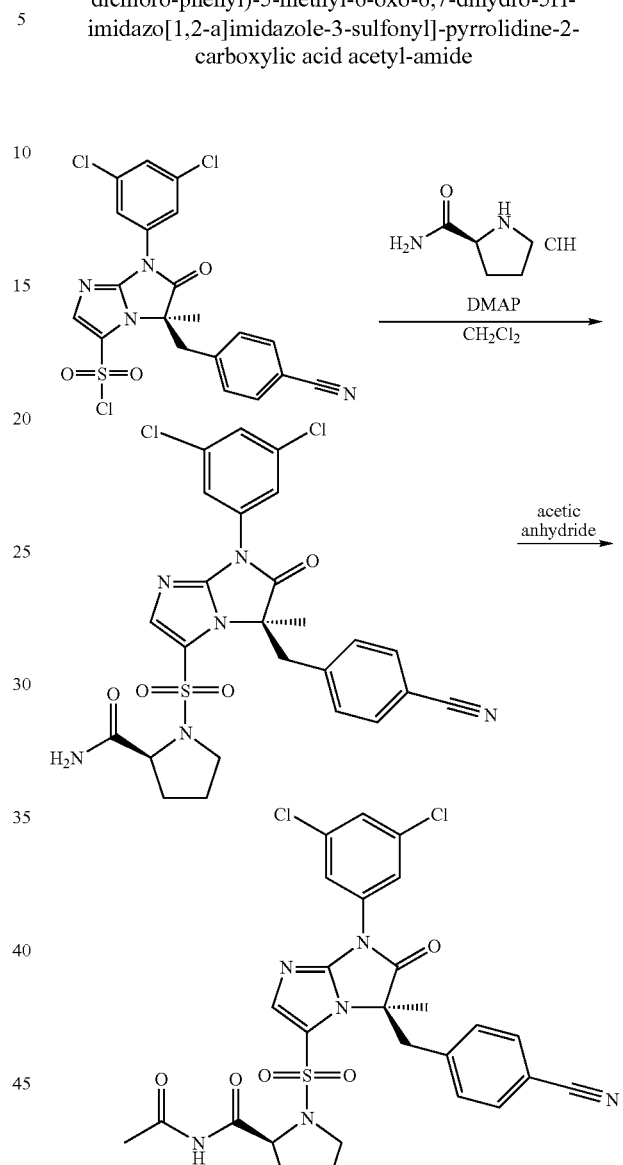

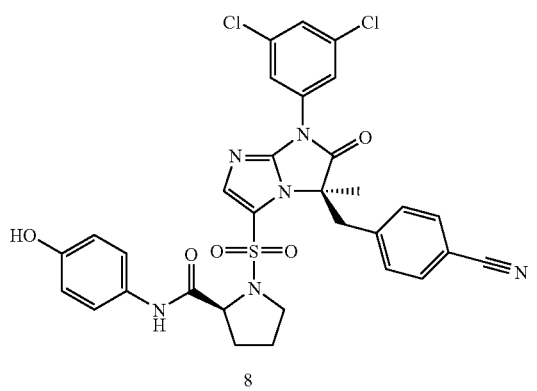

8

(S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (see Example 5) (122 mg, 0.2 mmol) was dissolved in methylene chloride (2 mL) under a nitrogen atmosphere. HATU (121 mg, 0.3 mmol) and DIPEA (111 µL, 0.64 mmol) were added. The t-butyldimethylsilyl-(TBDMS-) protected aniline (71 mg, 0.3 mmol) was added and the reaction was stirred overnight. The solvent was evaporated and the resulting residue chromatographed over silica gel (gradient EtOAc/hexanes) to provide a white solid. The white solid was dissolved in methylene chloride (2 mL) and a 1.0 M solution in THF of tetrabutylammonium fluoride (TBAF) (1 mL) was added and the reaction stirred for 3 h. Water and a few drops of 1 N HCl were added and the layers separated. The organic layer was dried over sodium sulfate, filtered, and evaporated. The resulting residue was chromatographed over silica gel (25% EtOAc in methylene chloride) to provide 83 mg of the title compound as a white solid (M+1, 665.2).

The following compound was made by procedures analogous to those described in the above example:

(S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (3-hydroxy-phenyl)-amide

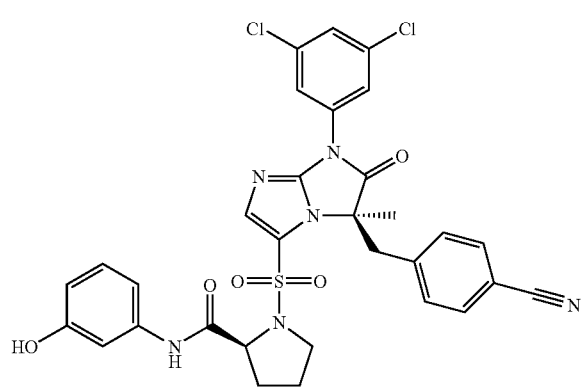

(M+1, 665).

9

To a stirred solution of (R)-5-(4-cyano-benzyl)-7-(3,5-dichloro-phenyl)-5-methyl-6-oxo-6,7-dihydro-5H-imidazo[1,2-a]imidazole-3-sulfonyl chloride (see Example 5) (50 mg, 0.10 mmol) in anhydrous methylene chloride (1 mL) was added 4-dimethylaminopyridine (DMAP) (37 mg, 0.30 mmol). L-Proline amide hydrochloride (69 mg, 0.30 mmol) was added to the mixture and the reaction was stirred for 18 h at room temperature under nitrogen. The reaction was concentrated and the residue was purified by column chromatography over silica gel (gradient elution with 35-50% EtOAc in hexanes) to provide 141 mg of (S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid amide as a white solid.

(S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid amide (98 mg, 0.17 mmol) was dissolved in acetic anhydride (3 mL, 0.05 M). The reaction was heated to 100° C. for 18 h. The mixture was concentrated, toluene added, and the mixture concentrated again. The residue was chromatographed over silica with a solvent system of 10% MeOH in methylene chloride to provide 19 mg of the title compound as a white solid (M+1, 615).

Example 10

Synthesis of (S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid ((R)-5-oxo-tetrahydro-furan-2-ylmethyl)-amide

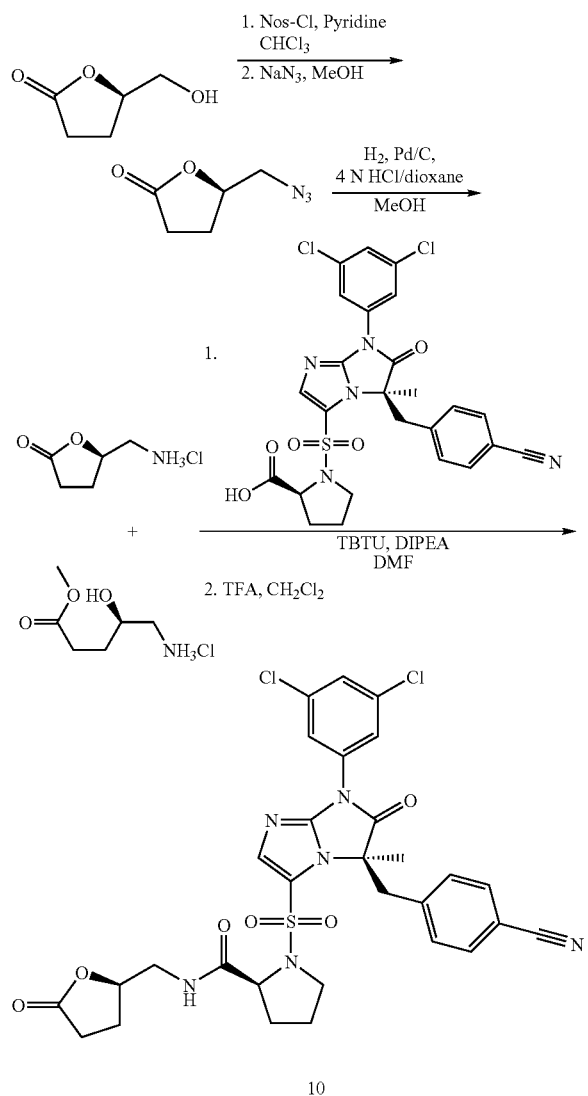

10

(R)-(−)-Dihydro-5-(hydroxymethyl)-2(3H)-furanone (2.0 g, 0.017 mol) was dissolved in CHCl$_3$ (20 mL) and cooled to 0° C. Pyridine (4.77 g, 0.060 mol) was added to the solution and stirred for 15 min. To this reaction solution, was added 4-nitrobenzenesulfonyl chloride (Nos-Cl) (4.6 g, 0.021 mol) and the reaction mixture was stirred at 0° C. for another 3 h. The reaction mixture was then washed with 1N HCl, saturated NaHCO$_3$ and water. The organic phase was dried over Na$_2$SO$_4$ and concentrated to afford the Nos-protected intermediate. This intermediate was characterized by $^1$H-NMR and then used directly for the next reaction. It was dissolved in MeOH (20 mL) and NaN$_3$ (5.6 g, 0.086 mol) was added to the solution. This heterogeneous reaction mixture was heated to 62° C. and stirred overnight. TLC indicated the reaction was not complete so the reaction mixture was stirred at 50° C. for 3 more days. The reaction mixture was then concentrated and the resulting residue was diluted with CH$_2$Cl$_2$, then washed with water to remove any remaining NaN$_3$. The organic phase was dried over Na$_2$SO$_4$ and concentrated. The desired (R)-(−)-dihydro-5-(azidoymethyl)-2(3H)-furanone was isolated by silica gel column chromatography using CH$_2$Cl$_2$ as an eluent.

The above intermediate (0.43 g) was dissolved in MeOH and Pd/C was added to the solution. The reaction mixture was saturated with H$_2$ and 4N HCl in dioxane was added to the mixture. The reaction mixture was stirred at room temperature for 2 h and then filtered through a diatomaceous earth pad. The filtrate was concentrated under reduced pressure to afford 0.4 g of a mixture of two products (furanone and hydroxy-ester) in hydrochloride salt form.

To a solution of (S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (see Example 5) (0.1 g, 0.174 mmol) in anhydrous DMF was added the above mixture of amines (0.030 g), followed by TBTU (0.084 g, 0.261 mmol) followed by DIPEA (0.075 mL, 0.435 mmol). The reaction mixture was stirred at room temperature for 30 min. The reaction mixture was then diluted with EtOAc and washed with water (×3), 1N HCl, and saturated NaHCO$_3$. The organic phase was dried over Na$_2$SO$_4$ and concentrated. The resulting residue was dissolved in CH$_2$Cl$_2$ and trifluoroacetic acid (1 eq) was added to the solution. The reaction mixture was stirred at room temperature for 3 h and washed with saturated NaHCO$_3$ and water. The organic phase was dried over Na$_2$SO$_4$ and concentrated. The resulting residue was purified by silica gel preparative thin layer chromatography using CH$_2$Cl$_2$-MeOH (95:5) as an eluent to afford 0.063 g of the title compound as a white foam (M+1, 671.1).

Example 11

Synthesis of (S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (2-hydroxy-2-methyl-propyl)-amide

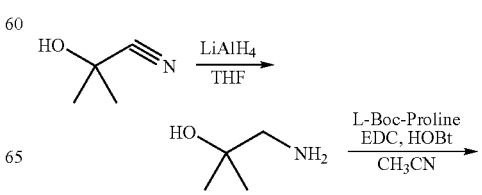

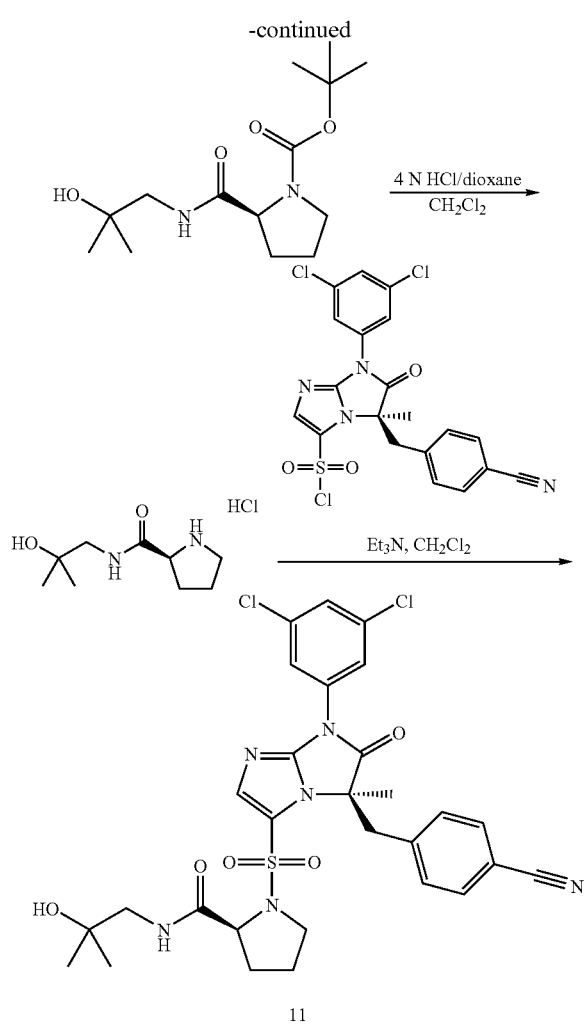

11

A 500 mL 3-necked round bottom flask was fitted with an overhead stirrer, a thermoprobe, and a Claisen head topped with a metering addition funnel and N₂ inlet. Lithium aluminum hydride (8.4 g) was placed in a flask and the flask was cooled in an ice bath. THF (150 mL) was added to the flask under N₂ stream. Gas was evolved and the internal temperature rose to ~50° C. The addition funnel was charged with 10 mL of acetone cyanohydrin in 50 mL of THF. After the internal temperature cooled to about 5° C., acetone cyanohydrin was added. The rate of addition was set to maintain the temperature below 10° C. The reaction mixture was allowed to gradually warm to room temperature and stir overnight. The reaction mixture was then cooled to about 5° C. and Na₂SO₄* 10H₂O was added in portions to maintain the temperature at about 10° C. After gas evolution and temperature increase stopped, the remaining amount was added and stirred in the ice bath for 30 min. The ice bath was removed and stirring continued overnight. The reaction mixture was filtered and the salts were washed with 200 mL of warm THF( about 50° C.). The filtrate was combined and concentrated to afford 5.6 g of 2-hydroxy-2-methyl-propyl-1-amine.

A solution mixture of L-Boc-proline (1.5 g, 7 mmol), 2-hydroxy-2-methyl-propyl-1-amine (1.24 g, 13.9 mmol) and HOBt (0.96 g, 7.1 mmol) in anhydrous acetonitrile (35 mL) was cooled down to 0° C. and EDC (1.6 g, 8.4 mmol) was added to the reaction mixture in one portion. The reaction mixture was allowed to warm to room temperature and stirred overnight. The solvent was removed, diluted with CH₂Cl₂ (30 mL) and washed with 5% citric acid (4×5 mL), saturated NaHCO₃ (4×5 mL) and brine. The organic layer was dried over Mg₂SO₄ and concentrated to afford 1.5 g of the amide.

The Boc-protected alcohol (0.31 g, 1.082 mmol) from above was dissolved in CH₂Cl₂ (5 mL) and 4N HCl in dioxane (5 mL) was added to the reaction solution. The reaction mixture was stirred at room temperature for 3 h and then concentrated under reduced pressure to afford 0.24 g of pyrrolidine-2-carboxylic acid (2-hydroxy-2-methyl-propyl)-amide hydrochloride.

Pyrrolidine-2-carboxylic acid (2-hydroxy-2-methyl-propyl)-amide hydrochloride (0.241 g, 1.082 mmol) was dissolved in CH₂Cl₂ and triethylamine (0.206 mL, 1.513 mmol) was added to the solution. The reaction mixture was stirred at room temperature for 10 min. (R)-5-(4-Cyano-benzyl)-7-(3,5-dichloro-phenyl)-5-methyl-6-oxo-6,7-dihydro-5H-imidazo[1,2-a]imidazole-3-sulfonyl chloride (see Example 5) (0.3 g, 0.605 mmol) in CH₂Cl₂ was added to the reaction mixture and stirred for 1 h. DMF (0.5 mL) was then added to the reaction mixture and stirred for another 30 min. The reaction solution was washed with 1N HCl and saturated NaHCO₃. The organic phase was dried over Na₂SO₄ and concentrated. The crude product was purified by silica gel preparative thin layer chromatography using CH₂Cl₂-MeOH (10:1) as an eluent to afford 0.28 g of the title compound (M+1, 644.98).

Example 12

Synthesis of (S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid carbamoylmethyl-amide

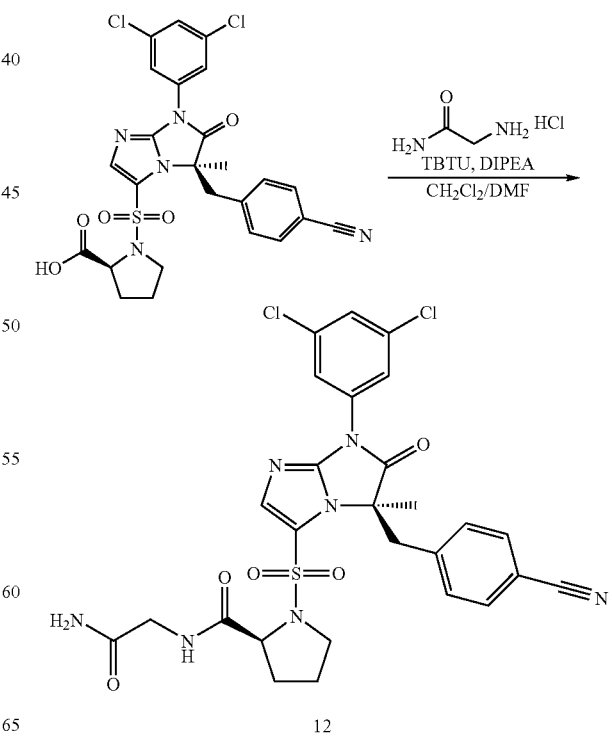

12

(S)-1-[(R)-5-(4-Cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (see Example 5) (0.25 g, 0.435 mmol) was dissolved in a mixture of $CH_2Cl_2$ (10 mL) and DMF (0.2 mL). To this solution, were added glycinamide hydrochloride (0.072 g, 0.653 mmol), TBTU (0.21 g, 0.653 mmol), and DIPEA (0.19 mL, 1.087 mmol). The reaction mixture was stirred at room temperature for 1 h. The reaction mixture was diluted with $CH_2Cl_2$ and washed with 1N HCl followed by saturated aq. $NaHCO_3$. The organic phase was dried over $Na_2SO_4$ and concentrated. The crude product was purified by silica gel preparative thin layer chromatography using $CH_2Cl_2$-MeOH (95:5) as an eluent to afford 0.155 g of the title compound as a white foam (M+1, 630).

Example 13

Synthesis of (S)-1-[(R)-5-(4-cyano-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid (2-hydroxy-ethyl)-amide

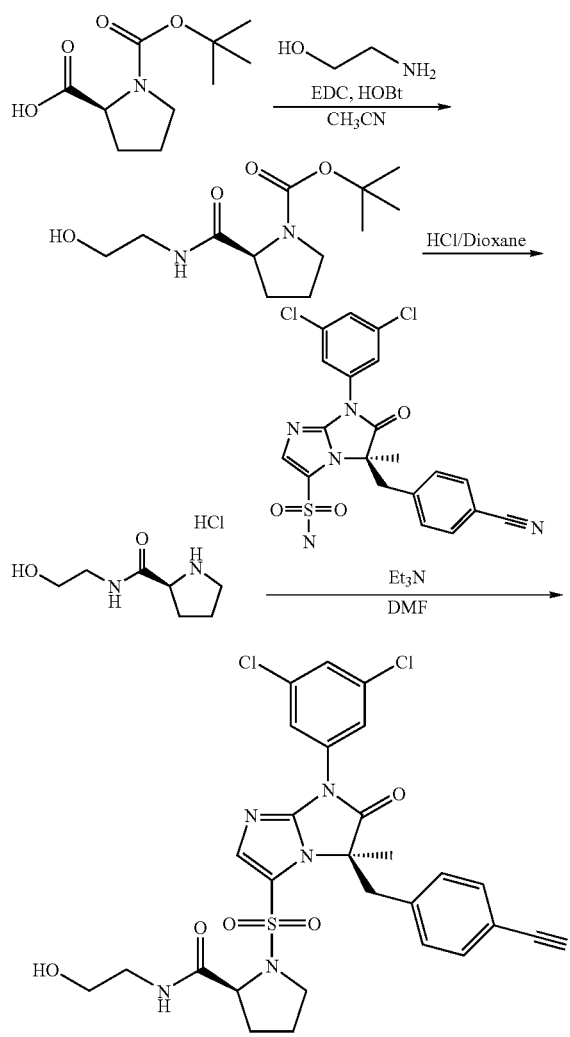

A mixture of L-Boc-proline (2.5 g, 11.6 mmol), HOBt (1.6 g, 11.8 mol) and ethanolamine (0.85 g, 13.9 mmol) in $CH_3CN$ was cooled to 0° C. To this heterogeneous reaction mixture, was added EDC (2.67 g, 13.9 mmol) in one portion. The reaction mixture was allowed to warm to room temperature and stirred overnight. The solvent was then evaporated and the residue was treated with EtOAc (100 mL). This organic solution was washed with 5% citric acid. The aqueous layer was saturated with NaCl and extracted with EtOAc (4×50 mL). The organic phase was combined and washed with saturated $NaHCO_3$ (10 mL), brine and dried over $Na_2SO_4$. The solution was concentrated and re-dissolved in $CH_2Cl_2$ (100 mL) and washed with saturated $NaHCO_3$ (10 mL) to remove residual HOBt. The organic phase was dried over $Na_2SO_4$ and concentrated to afford 2.53 g of the ethanolamine coupled proline derivative as a white solid.

The above intermediate (2.53 g) was dissolved in $CH_2Cl_2$ (30 mL) and 4N HCl in dioxane (7.3 mL) was added to the solution. The reaction solution was stirred at room temperature for 2 h. The reaction solution was bubbled with a strong stream of $N_2$ for 40 min and then concentrated in vacuo to afford the de-protected proline amine HCl salt as a solidified gummy residue.

The above amine HCl salt (0.93 g) was dissolved in anhydrous DMF (9 mL) by vigorously stirring at room temperature for 30 min. When all the amine salt was dissolved, triethylamine (1 mL) was added to the solution. (R)-5-(4-Cyano-benzyl)-7-(3,5-dichloro-phenyl)-5-methyl-6-oxo-6,7-dihydro-5H-imidazo[1,2-a]imidazole-3-sulfonyl chloride (see Example 5) (1.18 g) in anhydrous DMF (1 mL) was then added to the reaction mixture and stirred at room temperature for 30 min. The reaction mixture was then diluted with EtOAc and washed with water (×2), 1N HCl, saturated $NaHCO_3$ and brine. The organic phase was then dried over $Na_2SO_4$ and concentrated. The residue was purified by silica gel column chromatography using $CH_2Cl_2$ and MeOH (gradient 0-5% MeOH) as an eluent to afford 1.18 g of the title compound as a white foam (M+1, 617.2)

Example 14

Synthesis of (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid

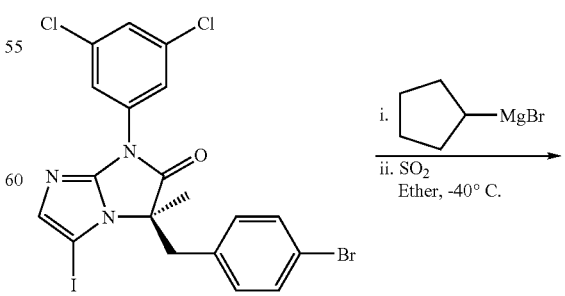

-continued

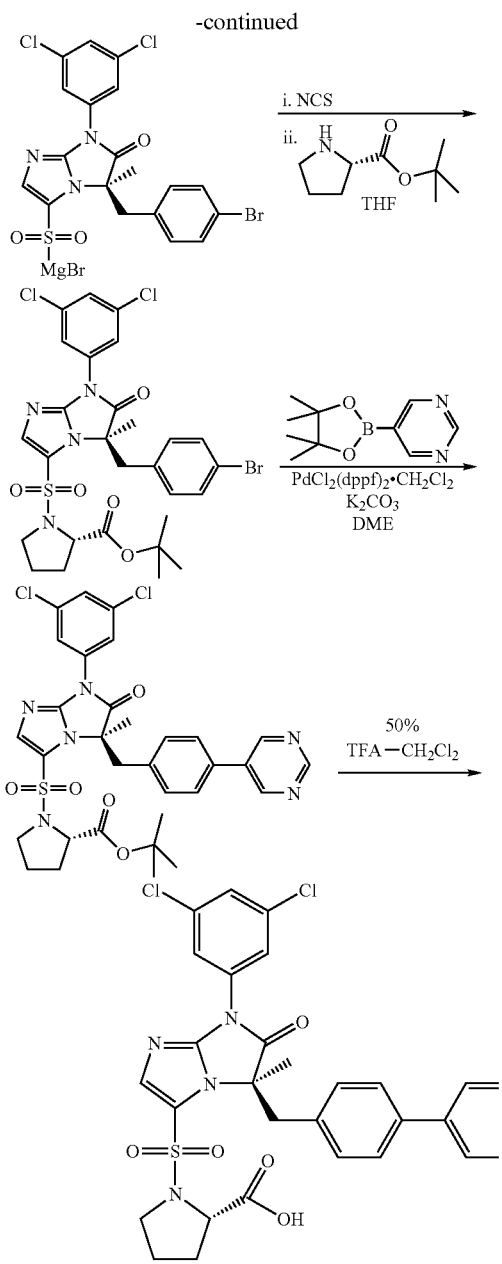

14

Cyclopentylmagnesium bromide (5.2 mL, 2 M solution in Et₂O) was added to a solution of (R)-3-(4-bromo-benzyl)-1-(3,5-dichloro-phenyl)-5-iodo-3-methyl-1H-imidazo[1,2-a]imidazol-2-one (5.0 g) in Et₂O (30 mL) at −40° C. and stirred for 15 min. SO₂ was bubbled through the reaction solution for 1 min and the reaction mixture was stirred for an additional 20 min then warmed to room temperature. The precipitate was isolated by filtration, washed with Et₂O and the remainder of the solvent was removed in vacuo. The resultant salt was dissolved in THF (10 mL) and added dropwise to a solution of N-chlorosuccinimide (0.86 g) in THF (20 mL) at −25° C. The reaction was allowed to slowly warm to room temperature and stirred for 1 h. L-Proline-tert-butyl ester (2.2 g) was added to the reaction solution and stirred for 2 h. The volatiles were removed and the resultant residue was re-dissolved in EtOAc and washed with 1 N HCl, followed by saturated NaHCO₃ and H₂O. The organic layers were combined, dried (Na₂SO₄), filtered and concentrated. The resultant residue was purified by silica gel chromatography to afford (S)-1-[(R)-5-(4-bromo-benzyl)-7-(3,5-dichloro-phenyl)-5-methyl-6-oxo-6,7-dihydro-5H-imidazo[1,2-a]imidazole-3-sulfonyl]-pyrrolidine-2-carboxylic acid tert-butyl ester.

To the above tert-butyl ester (2.0 g) in degassed dimethoxyethane (30 mL) was added 5-(4,4,5,5,-tetramethyl-[1,3,2]dioxaborolan-2-yl)-pyrimidine (1.2 g), K₂CO₃ (1.61 g), and PdCl₂(dppf)-CH₂Cl₂ (0.24 g). The reaction was heated to 95° C. for 24 h then cooled to room temperature and the volatiles were removed. The residue was diluted in CH₂Cl₂ and washed with H₂O. The organic layers were combined, dried (Na₂SO₄), filtered and concentrated. The resultant residue was purified by silica gel chromatography to afford (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid tert-butyl ester (1.5 g).

The above intermediate was dissolved in 50% trifluoroacetic acid-CH₂Cl₂ (30 mL) at 0° C. and allowed to slowly warm to room temperature. The reaction was allowed to stir for 1 h then concentrated to afford 1.2 g of the title compound.

Example 15

Synthesis of (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-methoxy-ethyl)-amide

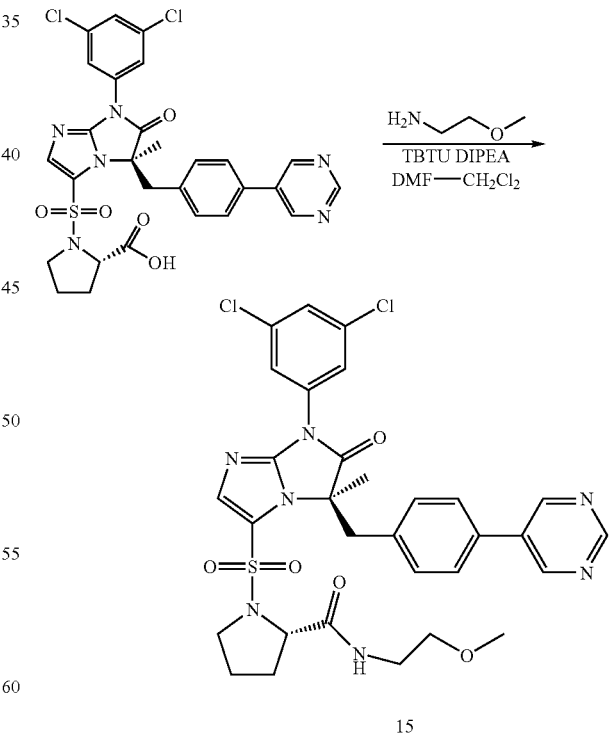

15

TBTU (0.077 g), DIPEA (0.090 mL) and (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (Example 14) (0.10 g)

were combined in 5% DMF-CH$_2$Cl$_2$ (4.2 mL) at room temperature. 2-Methoxyethylamine (0.036 g) was then added and the reaction solution was stirred overnight. The reaction was diluted with CH$_2$Cl$_2$, poured into 1N HCl, and extracted with CH$_2$Cl$_2$. The organic layers were subsequently extracted with CH$_2$Cl$_2$ from saturated aqueous NaHCO$_3$ followed by brine. The combined organic phase was dried (MgSO$_4$), filtered, and concentrated. The residue was purified by silica gel chromatography to afford 0.045 g of the title compound (684.2, M+1) as a foam.

Analogous procedures were employed to prepare the following compounds and utilized standard coupling reagents, such as TBTU, carbonyl diimidazole (CDI), or N-cyclohexylcarbodiimide; tertiary amines, such as Et$_3$N or DIPEA; and either the amine or amine hydrochloride:

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-acetylamino-ethyl)-amide (711.2, M+1):

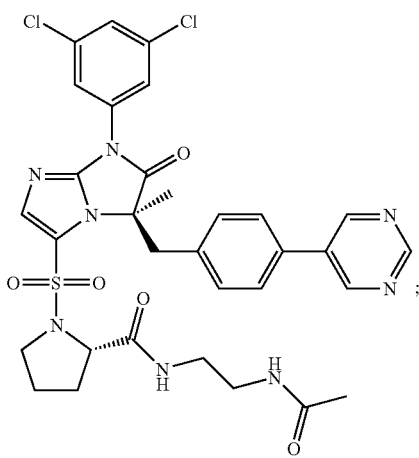

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-dimethylamino-ethyl)-amide (697.3, M+1):

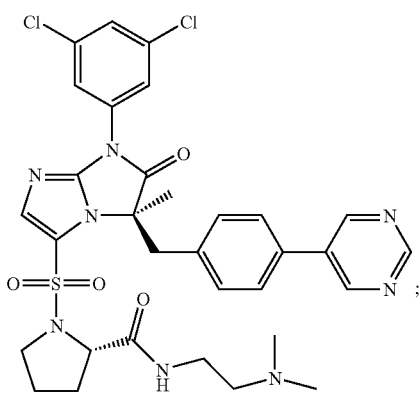

Acetic acid 2-({(S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-ethyl ester (712.2, M+1):

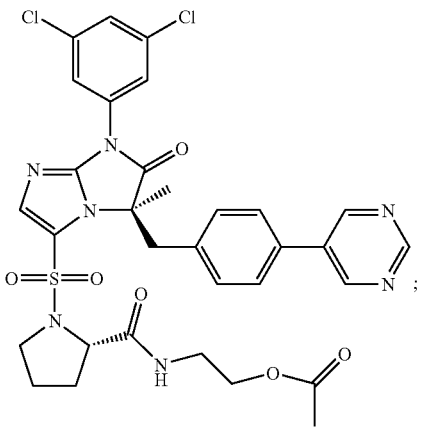

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-hydroxy-2-methyl-propyl)-amide (698.2, M+1):

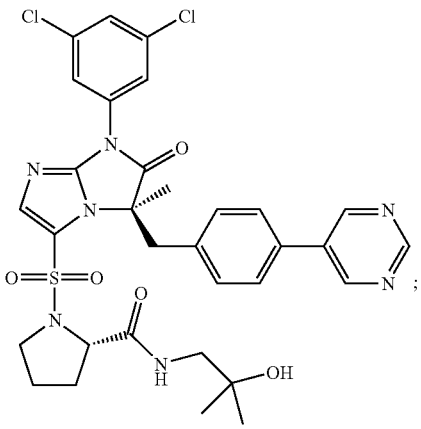

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-hydroxy-ethyl)-amide

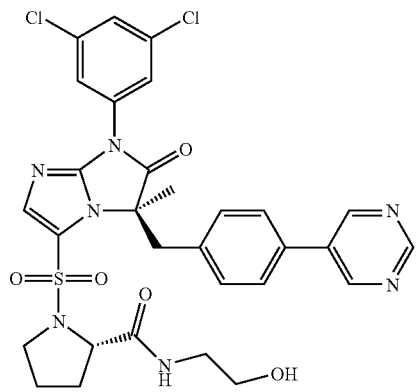

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-morpholin-4-yl-ethyl)-amide (739.3, M+1):

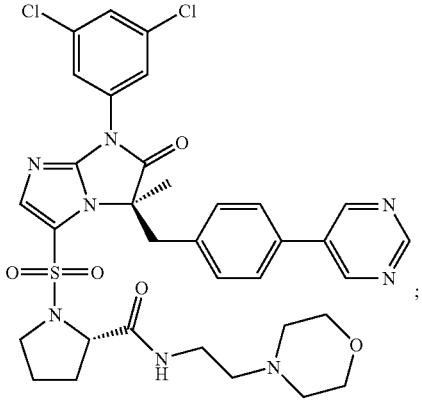

(R)-1-(3,5-Dichloro-phenyl)-5-[(S)-2-(3-hydroxy-piperidine-1-carbonyl)-pyrrolidine-1-sulfonyl]-3-methyl-3-(4-pyrimidin-5-yl-benzyl)-1H-imidazo[1,2-a]imidazol-2-one (710.3, M+1);

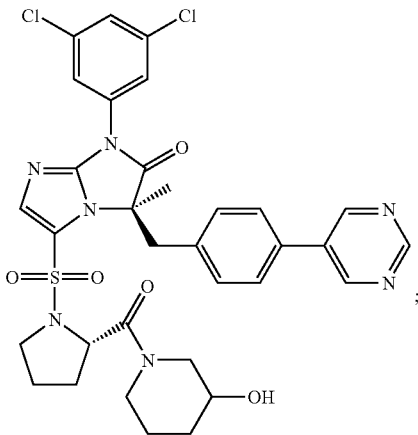

[2-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-ethyl]-carbamic acid tert-butyl ester (769.3, M+1):

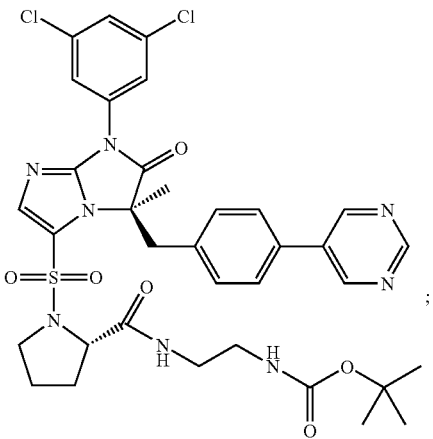

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-aminoethyl)-amide (669.3, M+1):

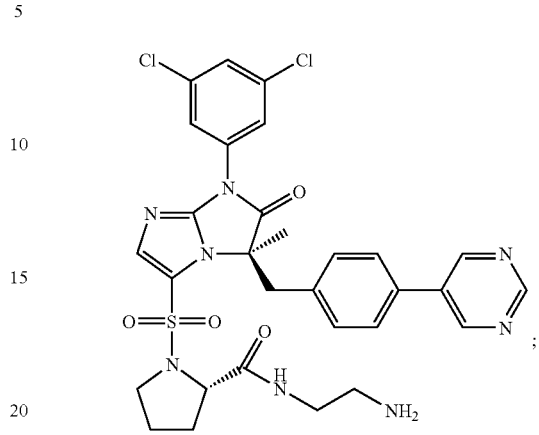

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (3-hydroxy-propyl)-amide (684.3, M+1):

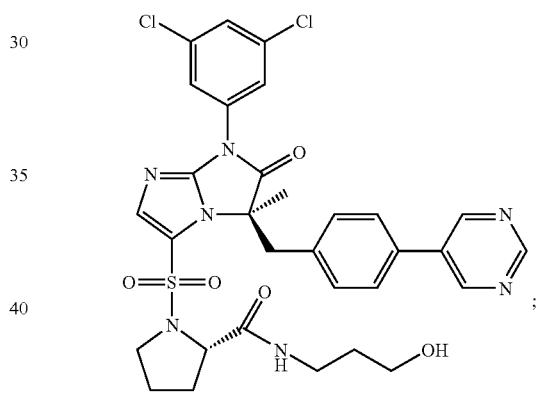

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (furan-2-ylmethyl)-amide (706.2, M+1):

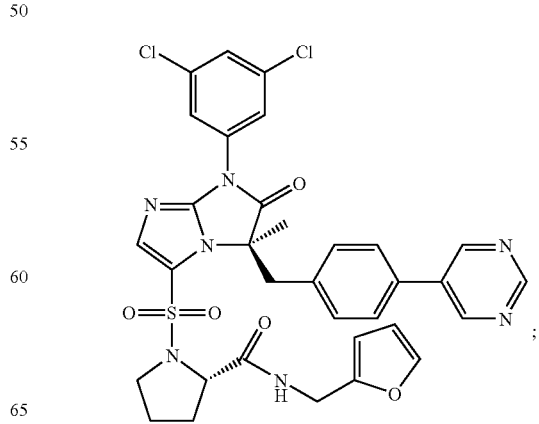

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2,3-dihydroxy-propyl)-amide (700.2, M+1):

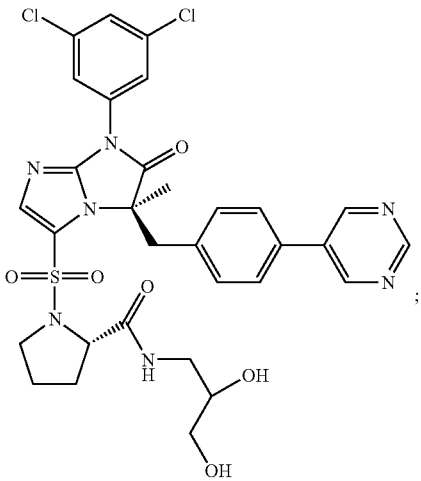

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-hydroxy-1-methyl-ethyl)-amide (684.2, M+1):

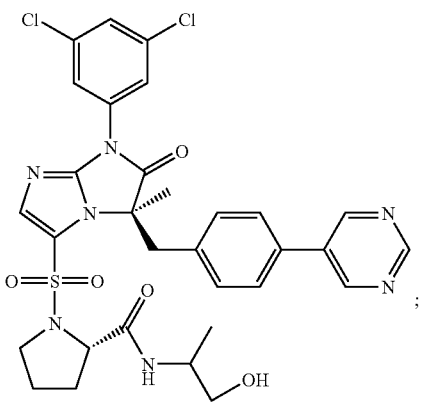

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid cyanomethyl-amide (665.2, M+1):

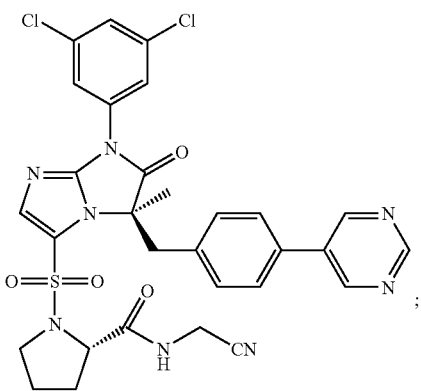

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid ((R)-2-hydroxy-1-methyl-ethyl)-amide (684.3, M+1):

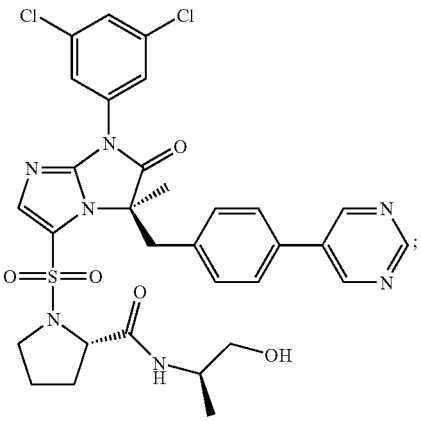

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid ((S)-1-hydroxymethyl-3-methyl-butyl)-amide (726.2, M+1):

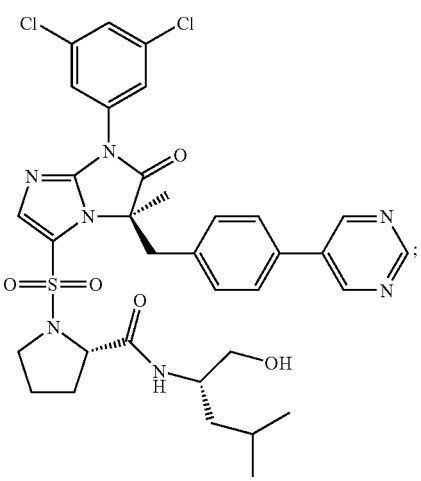

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid ((R)-1-hydroxymethyl-3-methyl-butyl)-amide (726.2, M+1):

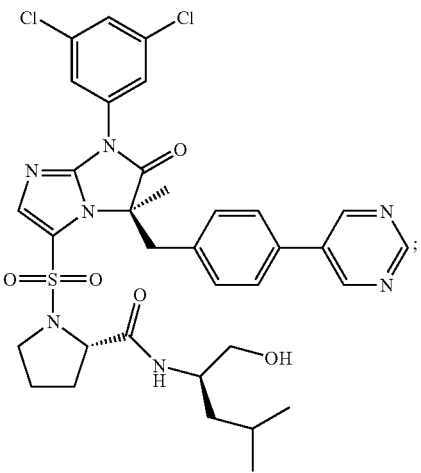

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-hydroxy-1-hydroxymethyl-ethyl)-amide (700.2, M+1):

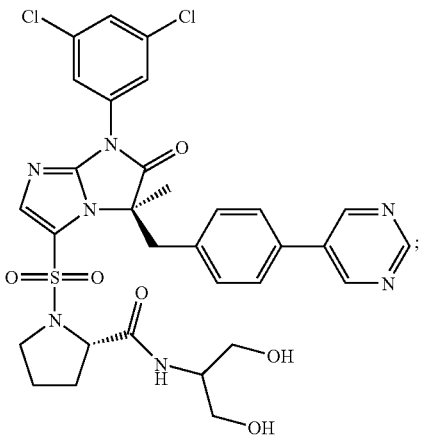

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-amino-phenyl)-amide (717.2, M+1):

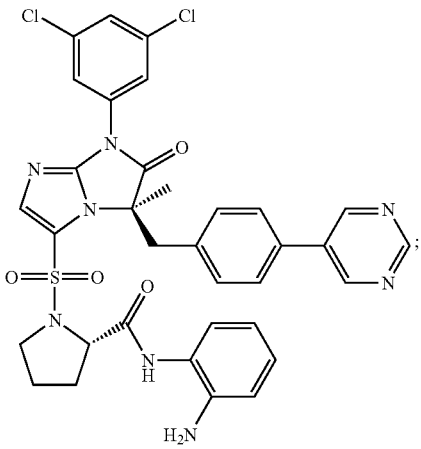

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (3-amino-phenyl)-amide (717.2, M+1):

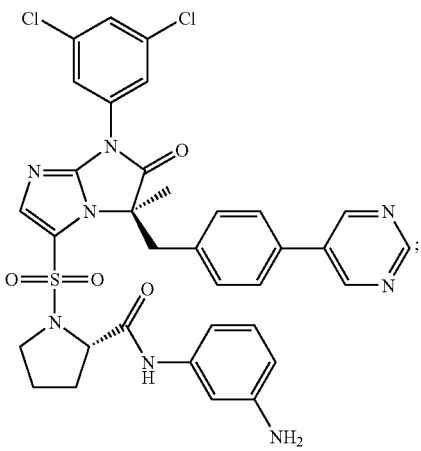

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (4-amino-phenyl)-amide (717.2, M+1):

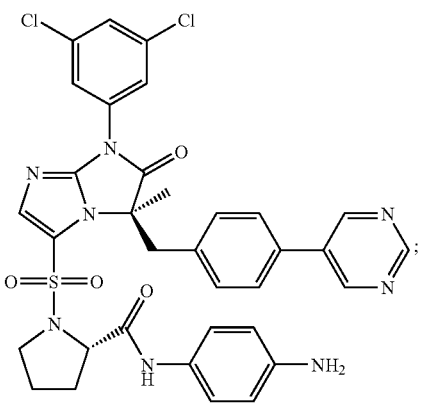

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid biphenyl-4-ylamide (778.2, M+1):

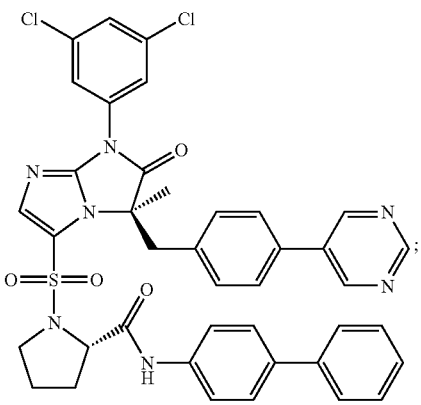

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid quinolin-6-ylamide (753.2, M+1):

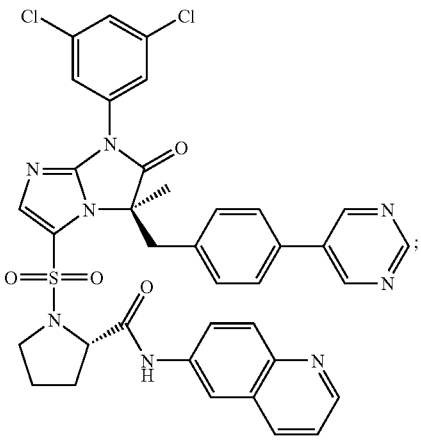

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (4-morpholin-4-yl-phenyl)-amide (787.2, M+1):

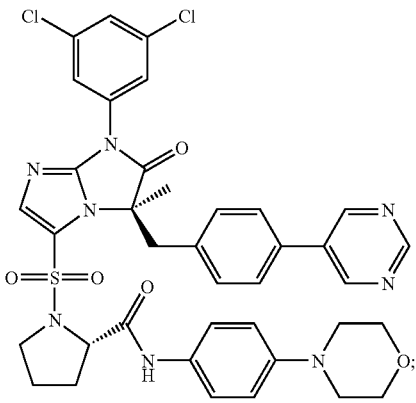

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (1-methyl-4-oxo-4,5-dihydro-1H-imidazol-2-yl)-amide (722.2, M+1):

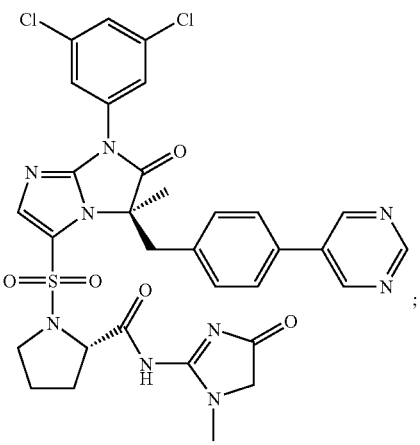

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (1,3,5-trimethyl-1H-pyrazol-4-yl)-amide (734.3, M+1):

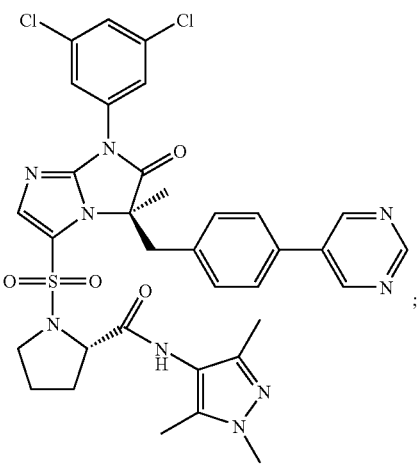

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (4-oxo-4,5-dihydro-thiazol-2-yl)-amide (725.2, M+1):

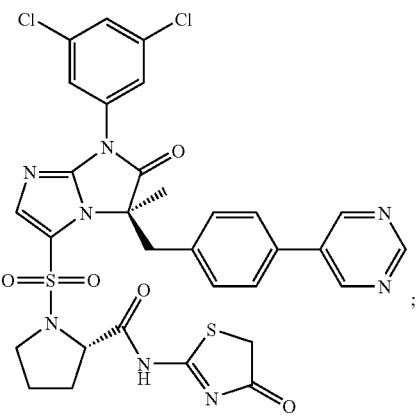

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid [1,3,4]thiadiazol-2-ylamide (710.1, M+1):

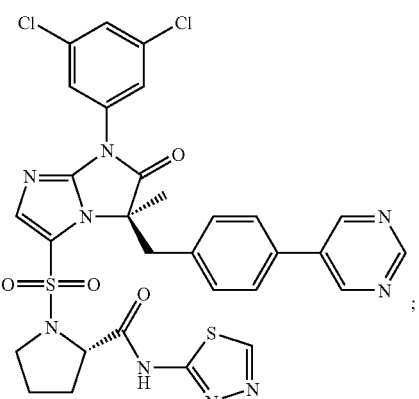

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-ethyl-2H-pyrazol-3-yl)-amide (720.3, M+1):

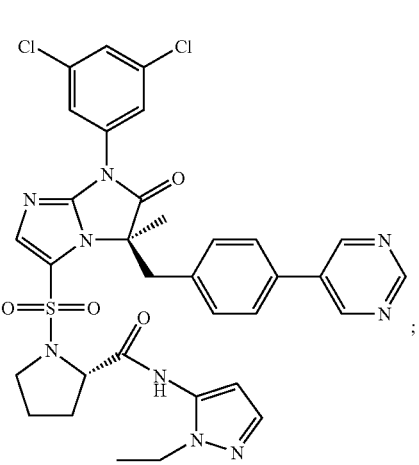

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-hydroxy-1,1-dimethyl-ethyl)-amide (698.1, M+1):

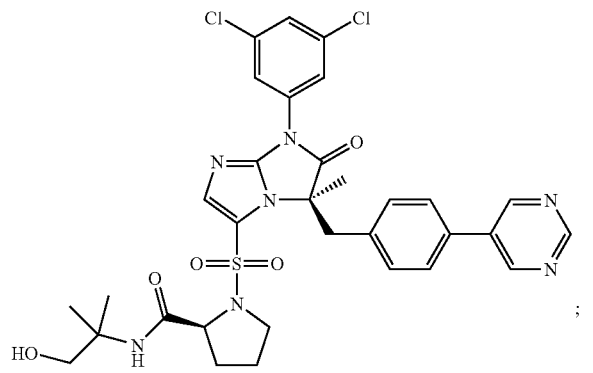

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid ((S)-2-hydroxy-propyl)-amide (684.0, M+1):

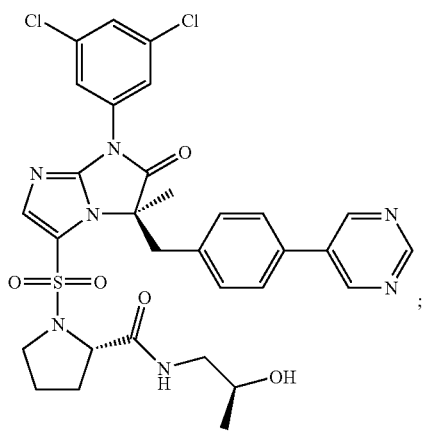

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid ((R)-2-hydroxy-propyl)-amide (684.0, M+1):

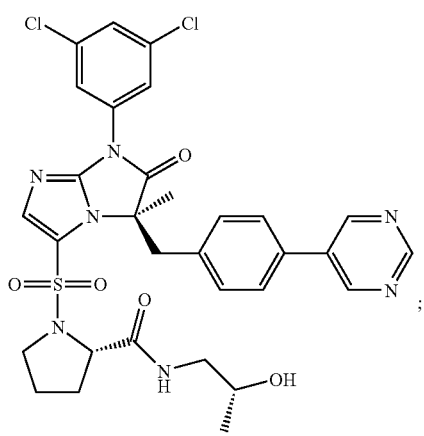

(R)-1-(3,5-Dichloro-phenyl)-5-[(S)-2-((R)-3-hydroxy-pyrrolidine-1-carbonyl)-pyrrolidine-1-sulfonyl]-3-methyl-3-(4-pyrimidin-5-yl-benzyl)-1H-imidazo[1,2-a]imidazol-2-one (696.2, M+1):

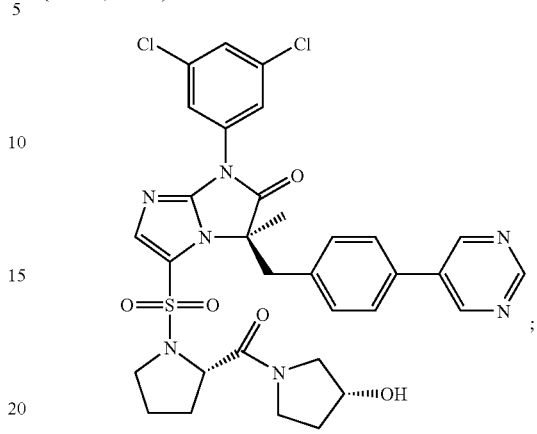

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid methylcarbamoylmethyl-amide (697.2, M+1):

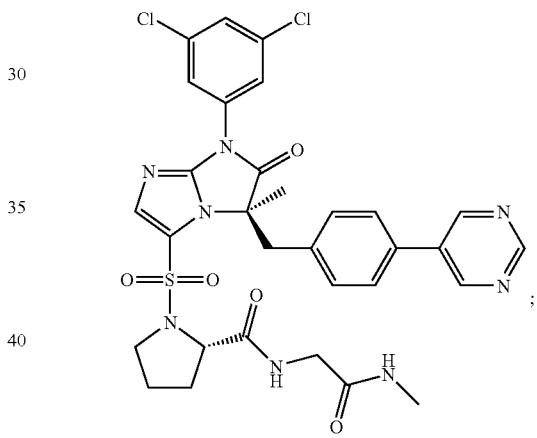

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid ((S)-1-methylcarbamoyl-ethyl)-amide (711.2, M+1):

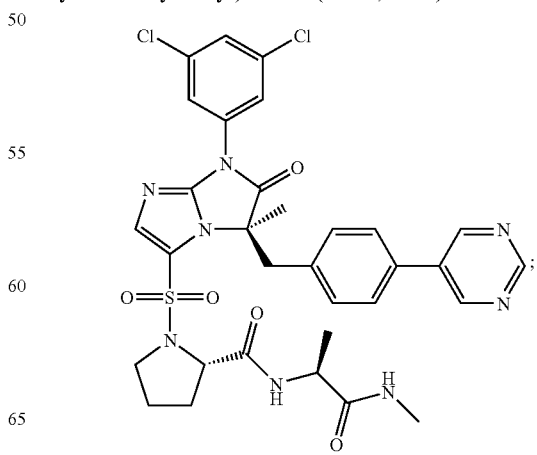

1-{(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-piperidine-4-carboxylic acid amide (737.3, M+1):

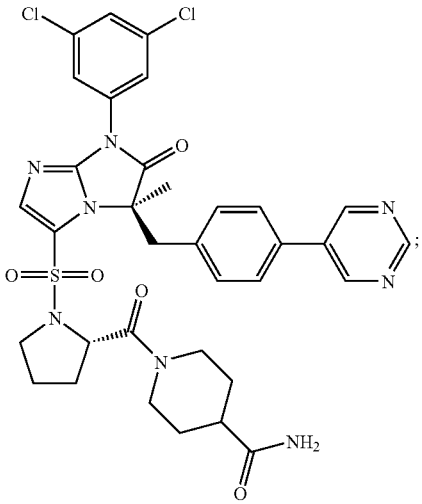

(R)-1-(3,5-Dichloro-phenyl)-5-[(S)-2-((S)-3-hydroxy-pyrrolidine-1-carbonyl)-pyrrolidine-1-sulfonyl]-3-methyl-3-(4-pyrimidin-5-yl-benzyl)-1H-imidazo[1,2-a]imidazol-2-one (696.2, M+1):

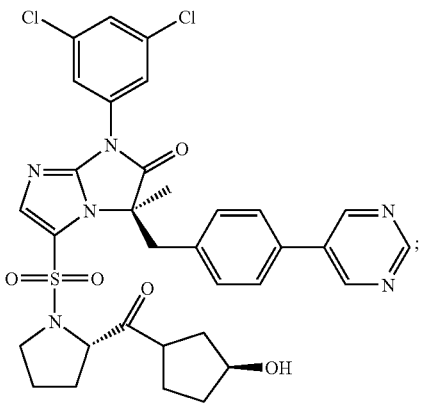

1-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-cyclopropanecarboxylic acid methyl ester (724.2, M+1):

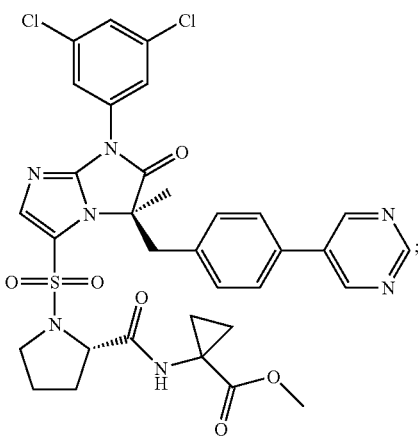

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (4,5-dihydro-oxazol-2-yl)-amide (695.0, M+1):

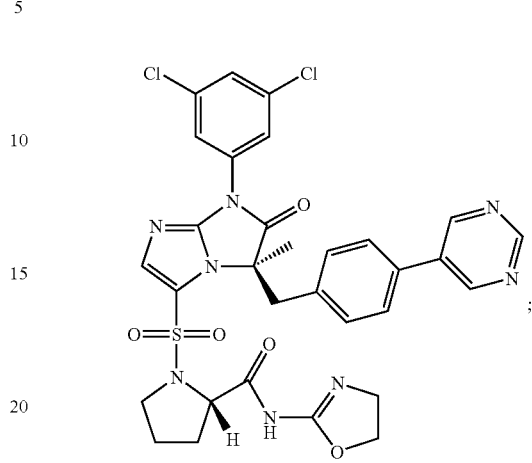

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (1H-tetrazol-5-ylmethyl)-amide (708.0, M+1):

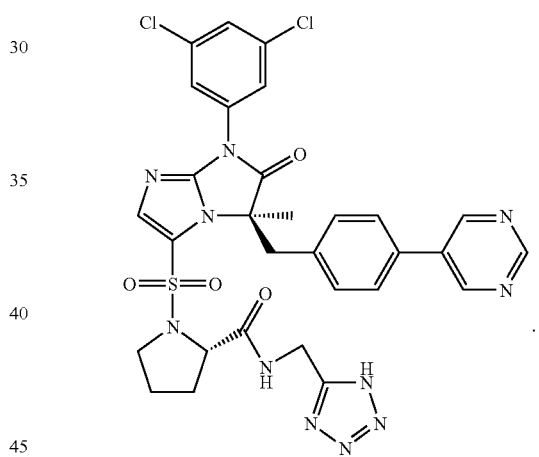

Example 16

Synthesis of (R)-2-({(S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-propionic acid

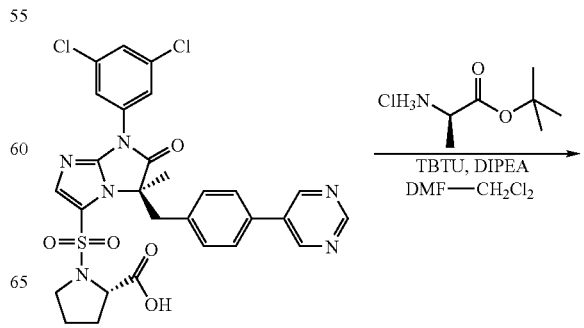

-continued

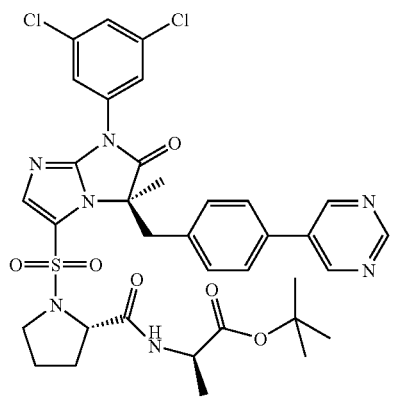

→ 50% TFA—CH₂Cl₂ or 4N HCl-dioxane (S)-2-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-propionic acid (698.3, M+1):

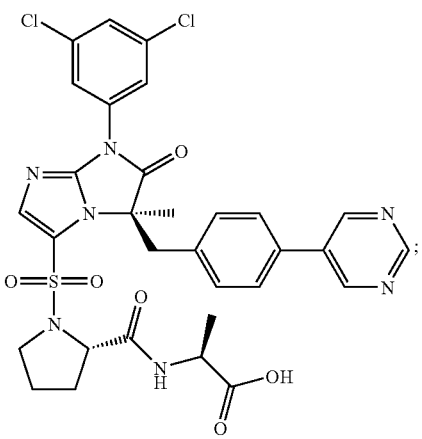

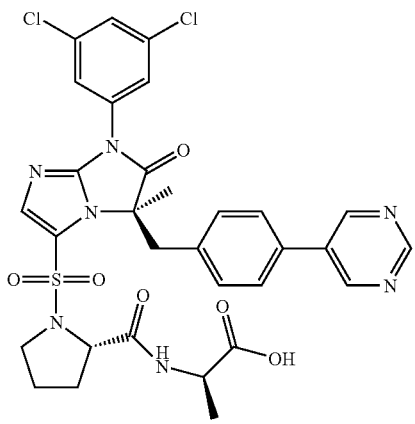

16

({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-acetic acid (683.9, M+1):

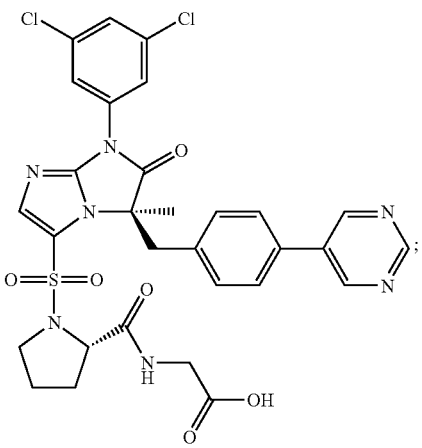

TBTU (0.078 g) and (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (Example 14) (0.10 g) were combined in 7% DMF-CH₂Cl₂ (3.2 mL) at room temperature. D-Alanine-tert-butyl ester hydrochloride (0.044 g), followed by DIPEA (0.07 mL), was then added and the reaction solution was stirred for 16 h. The reaction was diluted with CH₂Cl₂, poured into 1N HCl, and extracted with CH₂Cl₂. The organic layers were washed with saturated aqueous NaHCO₃ followed by H₂O. The combined organic phase was dried (MgSO₄), filtered and concentrated. The resultant residue was re-dissolved in either 50% trifluoroacetic acid-CH₂Cl₂ or 4N HCl-dioxane (5 mL) and stirred at room temperature for 2 h. Following aqueous workup the residue was purified by silica gel chromatography to afford the title compound (0.045 g) as a foam (698.9, M+1).

Analogous procedures were employed to prepare the following compounds and utilized standard coupling reagents, such as TBTU, CDI, or N-cyclohexylcarbodiimide, and tertiary amines, such as Et₃N or DIPEA:

({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-methyl-amino)-acetic acid (698.1, M+1):

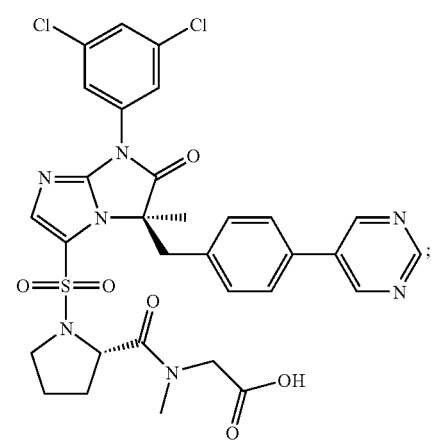

2-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-2-methyl-propionic acid (712.1, M+1):

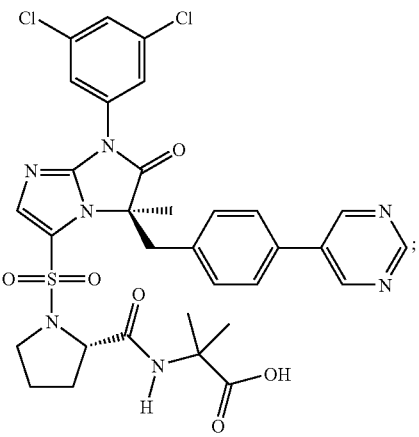

3-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-propionic acid (698.0, M+1):

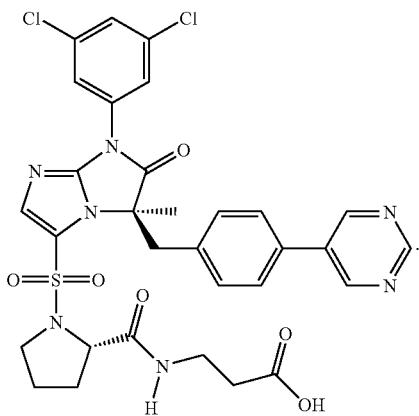

Example 17

Synthesis of 1-{(S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-piperidine-4-carboxylic acid

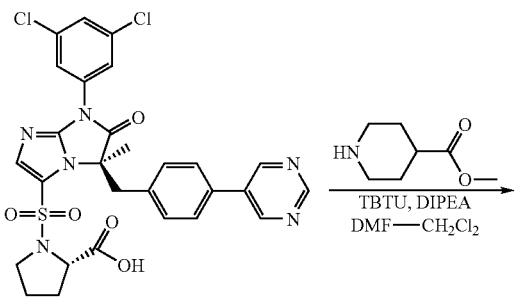

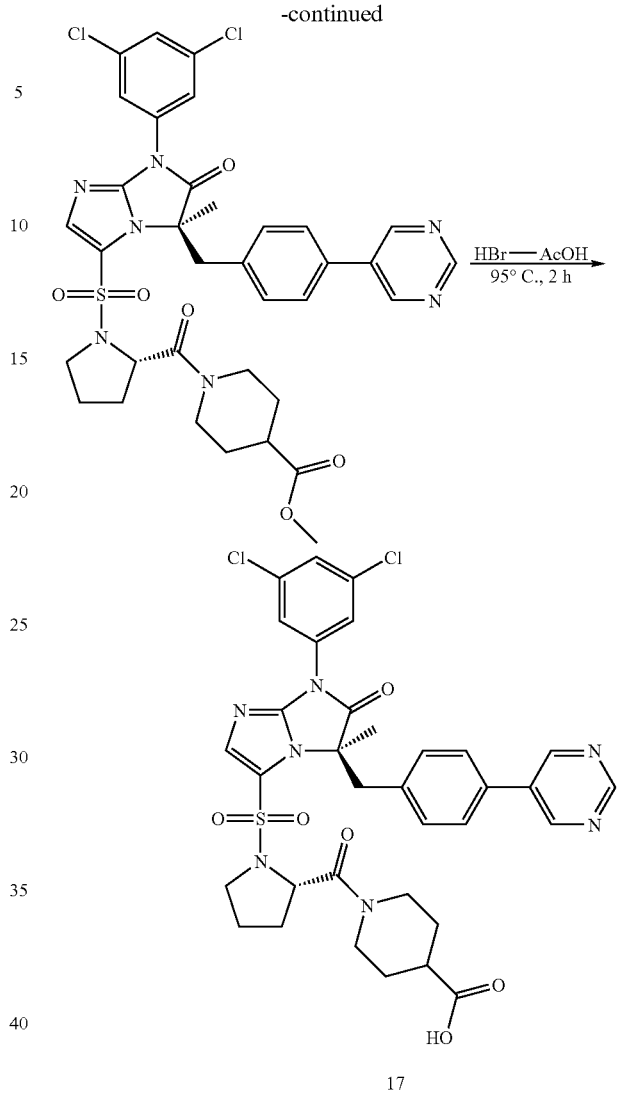

TBTU (0.12 g), (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (Example 14) (0.15 g) and methyl isonipecotate (0.041 g), followed by DIPEA (0.10 mL), were combined in 1% DMF-CH$_2$Cl$_2$ (10.1 mL) at room temperature and the solution was stirred for 1 h. The reaction was diluted with CH$_2$Cl$_2$, poured into 1N HCl, and extracted with CH$_2$Cl$_2$. The combined organic layers were washed with saturated aqueous NaHCO$_3$ followed by H$_2$O. The organic phase was dried (Na$_2$SO$_4$), filtered and concentrated. The resultant residue was re-dissolved in 30% HBr—AcOH and heated to 95° C. for 3 h. Following aqueous workup, the organic layer was dried (Na$_2$SO$_4$), filtered, concentrated, and the residue was purified by silica gel chromatography to afford the title compound (0.099 g) (738.2, M+1).

Analogous procedures were employed to prepare the following compounds and utilized standard coupling reagents, such as TBTU, CDI, or N-cyclohexylcarbodiimide; tertiary amines, such as Et$_3$N or DIPEA; and an amino acid as either the methyl or ethyl ester.

3-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-4,4,4-trifluoro-butyric acid (766.3, M+1):

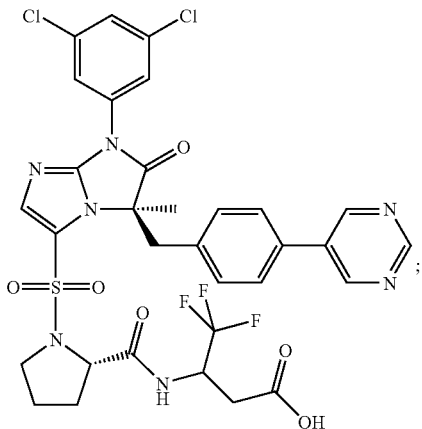

(S)-2-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-methyl-amino)-3-methyl-butyric acid (740.3, M+1):

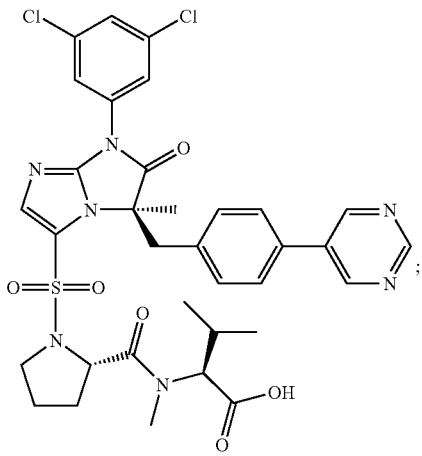

(1S,2S)-2-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-cyclohexanecarboxylic acid (752.2, M+1):

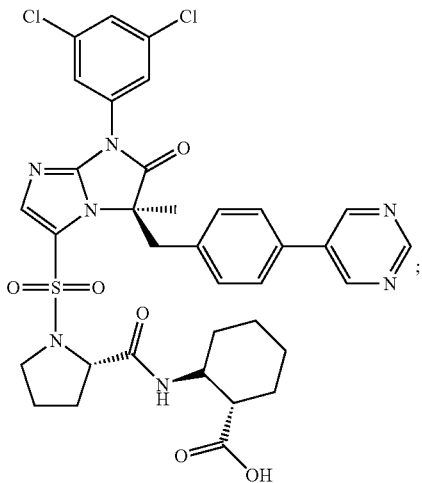

3-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-butyric acid (712.1, M+1);

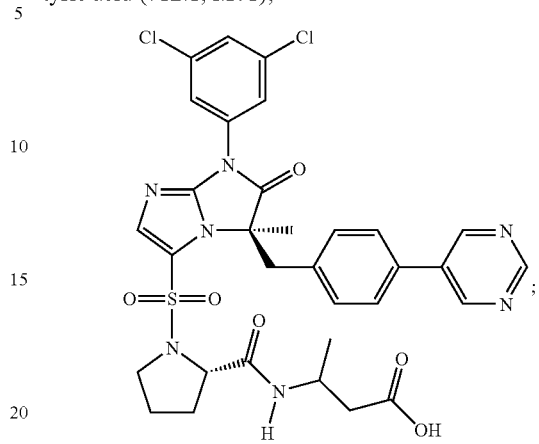

3-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-2-methyl-propionic acid (712.0, M+1):

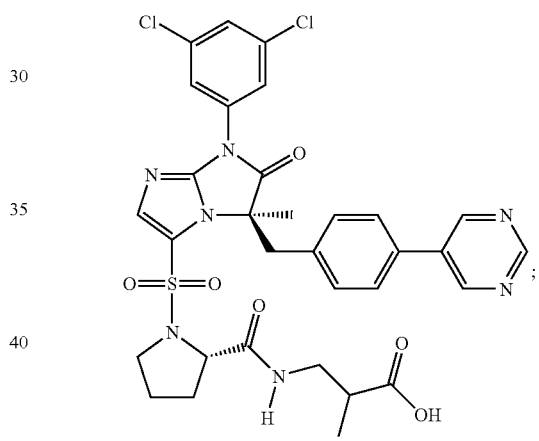

1-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-cyclopropanecarboxylic acid (710.1, M+1):

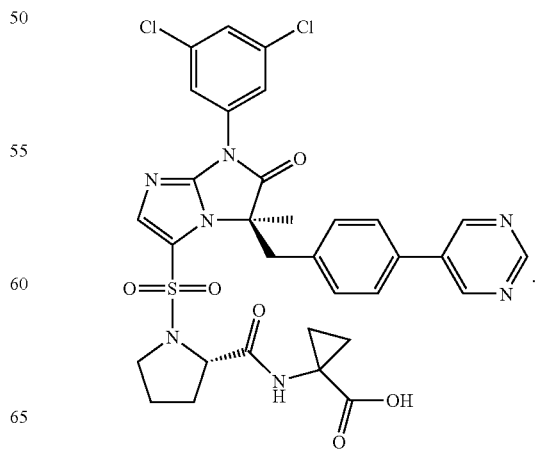

Example 18

Synthesis of (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (2-carbamoyl-ethyl)-amide

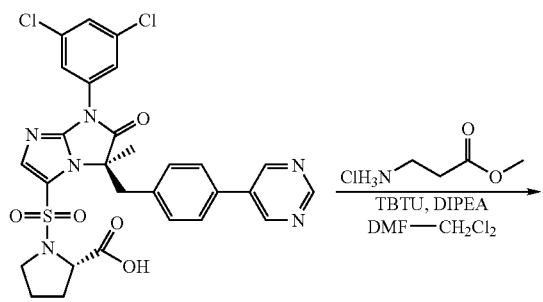

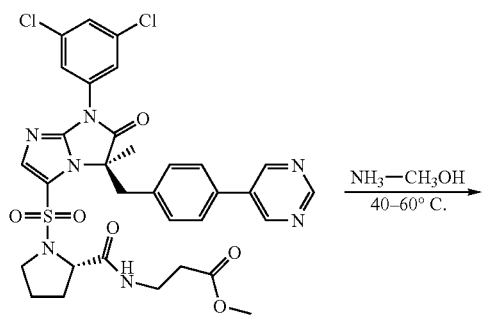

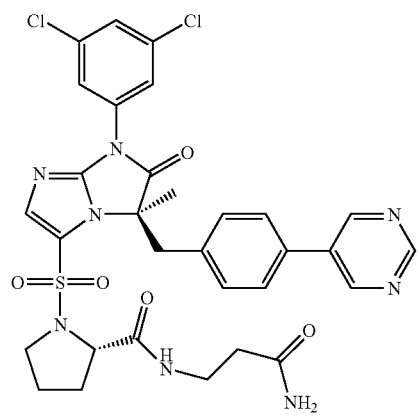

18

TBTU (0.15 g), (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (Example 14) (0.20 g), β-alanine methyl ester (0.067 g) and DIPEA (0.14 mL) were combined in 1% DMF-CH$_2$Cl$_2$ (10.1 mL) at room temperature and the solution was stirred for 1 h. The reaction was diluted with CH$_2$Cl$_2$, poured into 1N HCl, and extracted with CH$_2$Cl$_2$. The organic layers were combined and washed with saturated aqueous NaHCO$_3$ followed by H$_2$O. The combined organic phase was dried (Na$_2$SO$_4$), filtered and concentrated. The resultant residue was re-dissolved in 2N NH$_3$—CH$_3$OH (10 mL) and heated to 40-60° C. for 48 h. The volatiles were removed and the residue was purified by silica gel chromatography to afford the title compound (0.021 g) as a foam (697.2, M+1).

Example 19

Synthesis of (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid ((R)-1-carbamoyl-ethyl)-amide

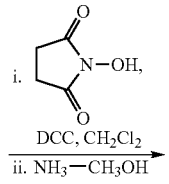

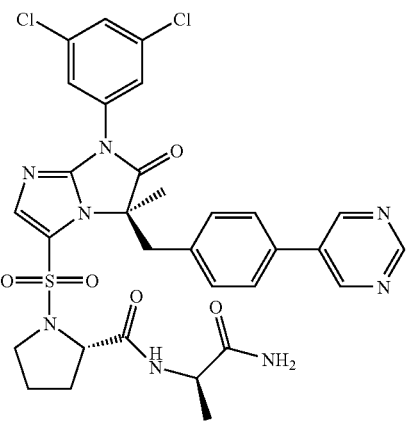

19

N-Hydroxysuccinimide (0.035 g), followed by 1,3-dicyclohexylcarbodiimide (DCC, 0.064 g), were added to a solution of (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (Example 14) (0.16 g) in CH$_2$Cl$_2$ (20 mL). The reaction was stirred at room temperature for 1 h, then was filtered through a pad of diatomaceous earth, concentrated and re-dissolved in 2N NH$_3$—CH$_3$OH (10 mL). The solution was stirred at room temperature for 1 h. The volatiles were then removed and the resultant residue was re-dissolved in CH$_2$Cl$_2$ and washed with H$_2$O. The combined organic layers were concentrated and the resultant residue was purified by silica gel chromatography to afford the title compound (0.128 g) as a foam (697.2, M+1).

The following compounds were prepared by procedures analogous to those described in the above example:

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid carbamoylmethyl-methyl-amide (697.3, M+1):

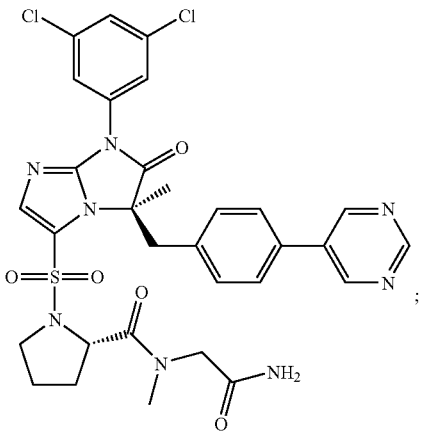

(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (1-carbamoyl-1-methyl-ethyl)-amide (711.2, M+1):

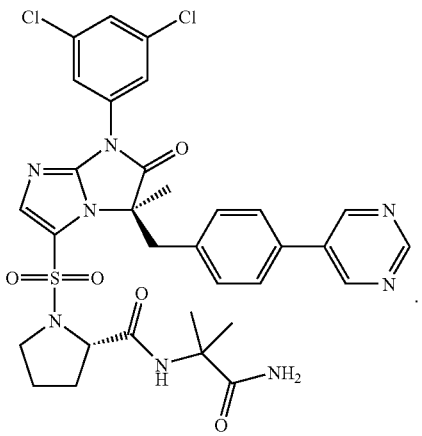

Example 20

Synthesis of (S)-2-({(S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-3-hydroxy-propionic acid

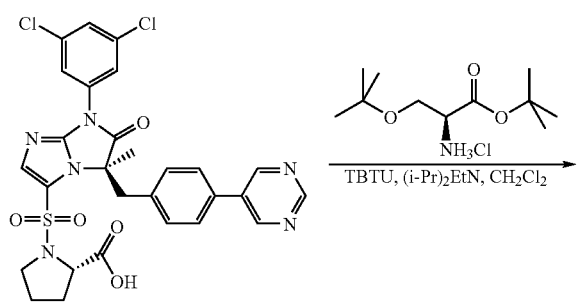

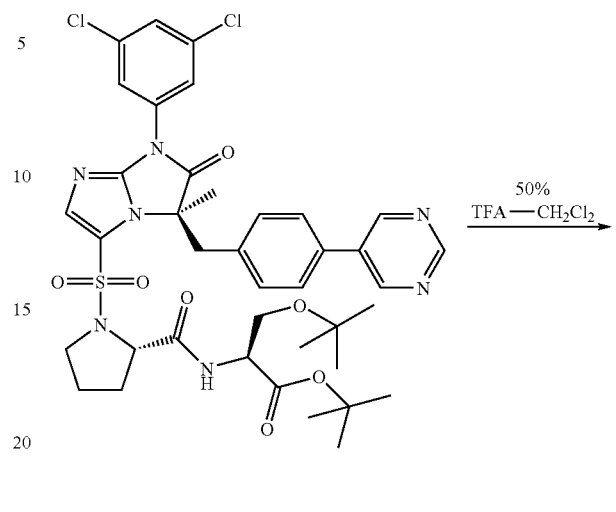

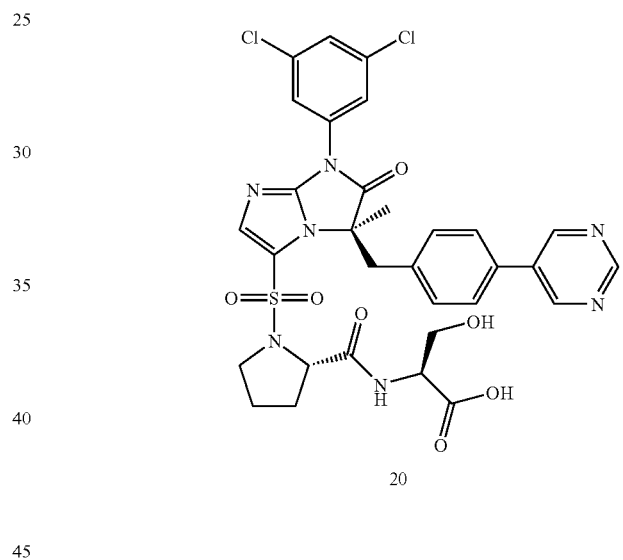

TBTU (0.077 g), DIPEA (0.1 ml), (S)-1-[(R)-7-(3,5-dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carboxylic acid (Example 14) (0.075 g) and O-tert-butyl-L-serine tert-butyl ester (0.061 g) were combined in 1:4 DMF-CH$_2$Cl$_2$ (1.2 mL) at room temperature and stirred for 2 h. The reaction was diluted with CH$_2$Cl$_2$ and extracted with 1 N HCl, followed by saturated aqueous NaHCO$_3$ and brine. The combined organic layers were dried (MgSO$_4$), filtered and concentrated. The resultant residue was purified by silica gel chromatography to afford the desired ester (0.099 g).

The above ester (0.099 g) was dissolved in 50% trifluoroacetic acid-CH$_2$Cl$_2$ (2 mL) and stirred for 24 h at room temperature. The volatiles were removed and the resultant residue was purified by silica gel chromatography to afford the title compound (0.064 g) as a foam (714.2, M+1).

The following compound was prepared by procedures analogous to those described for the above example:

(R)-2-({(S)-1-[(R)-7-(3,5-Dichloro-phenyl)-5-methyl-6-oxo-5-(4-pyrimidin-5-yl-benzyl)-6,7-dihydro-5H-imidazo[1,2-a]imidazole-3-sulfonyl]-pyrrolidine-2-carbonyl}-amino)-3-hydroxy-propionic acid (714.6, M+1):

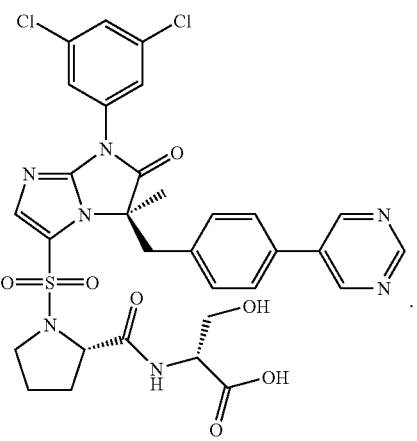

Example 21

Synthesis of (S)-1-[(R)-5-[4-(4-amino-pyrimidin-5-yl)-benzyl]-7-(3,5-dichloro-phenyl)-5-methyl-6-oxo-6,7-dihydro-5H-imidazo[1,2-a]imidazole-3-sulfonyl]-pyrrolidine-2-carboxylic acid (2-hydroxy-2-methyl-propyl)-amide

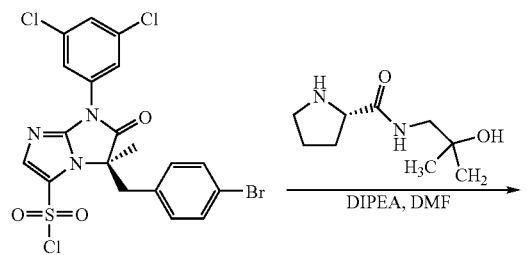

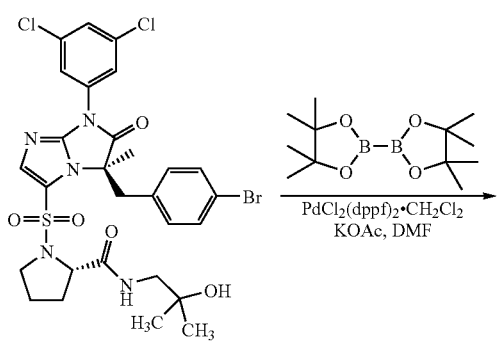

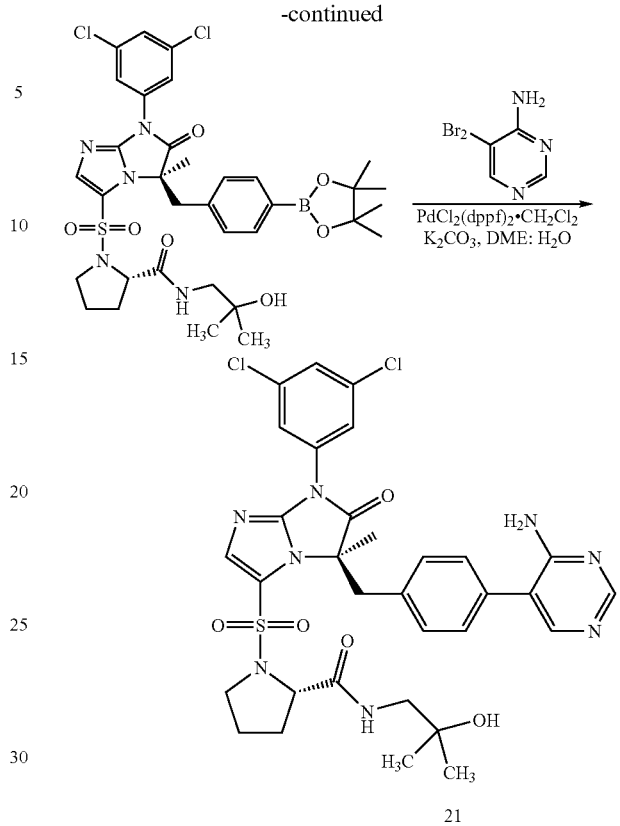

To a stirred solution of (R)-5-(4-bromo-benzyl)-7-(3,5-dichloro-phenyl)-5-methyl-6-oxo-6,7-dihydro-5H-imidazo[1,2-a]imidazole-3-sulfonyl chloride (see Example 14) (1.5 g) in a mixture of $CH_2Cl_2$ (25 mL) and anhydrous DMF (5 mL) was added L-Pyrrolidine-2-carboxylic acid (2-hydroxy-2-methyl-propyl)-amide (0.84 g) followed by N,N-diisopropylethylamine (1.5 mL). The reaction was stirred at room temperature for 2 h then diluted with EtOAc, washed with 1N HCl, $H_2O$ and brine. The combined organic layers were dried ($MgSO_4$), filtered and concentrated. The residue was purified by silica gel chromatography to afford the desired product (1.58 g).

To a stirred solution of the above amide (1.2 g) in DMF (80 mL) was added bis(pinacolato)diboron (0.871 g) followed by potassium acetate (0.674 g). The mixture was degassed for 10 min, then $PdCl_2(dppf) \cdot CH_2Cl_2$ (0.140 g) was added and the reaction mixture was heated at 80° C. After 36 h, the mixture was cooled to room temperature, diluted with $H_2O$, then extracted with EtOAc. The combined organic layers were washed with $H_2O$ and brine, then dried ($MgSO_4$), filtered and concentrated. The residue was purified by silica gel chromatography to afford the desired boronate (0.586 g).

The above boronate (0.2 g) was dissolved in DME:$H_2O$ (5 mL: 1 mL). 2-Amino-3-bromo-pyrimidine (0.070 g) and potassium carbonate (0.092 g) were added and the flask was flushed with $N_2$. The mixture was stirred for 20 min, and then $PdCl_2(dppf) \cdot CH_2Cl_2$ (0.020 g) was added. The mixture was heated at 80° C. for 2 h, cooled to room temperature and diluted with EtOAc. The mixture was filtered, concentrated and the residue was purified by silica gel chromatography to afford the title compound (0.080 g) as a foam (713.3, M+1)

The following compounds were prepared by procedures analogous to those described for the above example:

(S)-1-{(R)-7-(3,5-Dichloro-phenyl)-5-[4-(2-fluoro-pyrimidin-5-yl)-benzyl]-5-methyl-6-oxo-6,7-dihydro-5H-imidazo[1,2-a]imidazole-3-sulfonyl}-pyrrolidine-2-carboxylic acid (2-hydroxy-2-methyl-propyl)-amide (716.3, M+1):

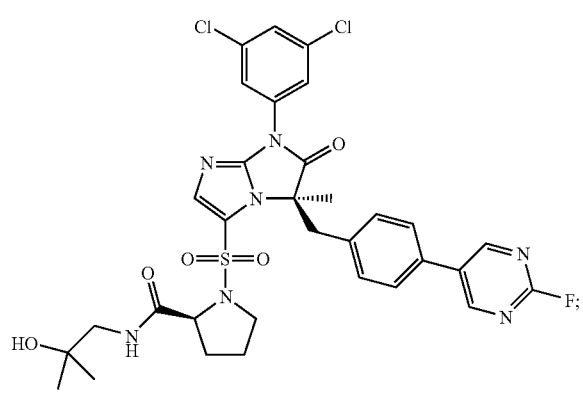

S)-1-[(R)-5-[4-(4-Amino-pyrimidin-5-yl)-benzyl]-7-(3,5-dichloro-phenyl)-5-methyl-6-oxo-6,7-dihydro-5H-imidazo[1,2-a]imidazole-3-sulfonyl]-pyrrolidine-2-carboxylic acid (2-hydroxy-ethyl)-amide (685.1, M+1):

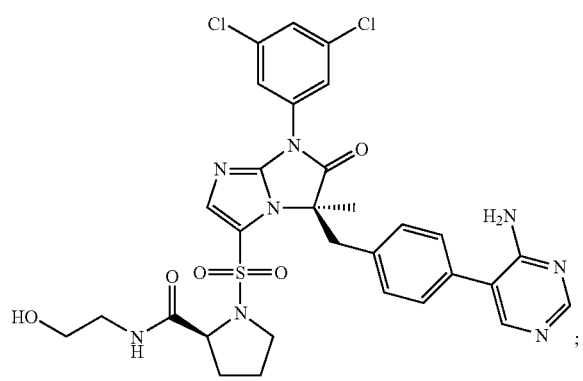

(S)-1-{(R)-7-(3,5-Dichloro-phenyl)-5-[4-(2-fluoro-pyrimidin-5-yl)-benzyl]-5-methyl-6-oxo-6,7-dihydro-5H-imidazo[1,2-a]imidazole-3-sulfonyl}-pyrrolidine-2-carboxylic acid (2-hydroxy-ethyl)-amide (688.0, M+1):

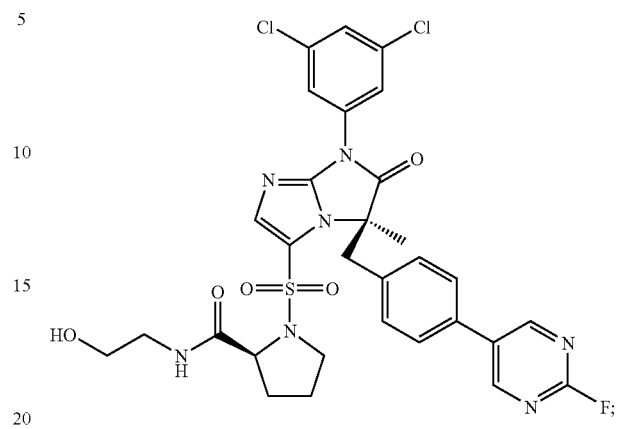

(S)-1-[(R)-5-[4-(2-Cyano-pyridin-3-yl)-benzyl]-7-(3,5-dichloro-phenyl)-5-methyl-6-oxo-6,7-dihydro-5H-imidazo[1,2-a]imidazole-3-sulfonyl]-pyrrolidine-2-carboxylic acid (2-hydroxy-2-methyl-propyl)-amide (722.1, M+1):

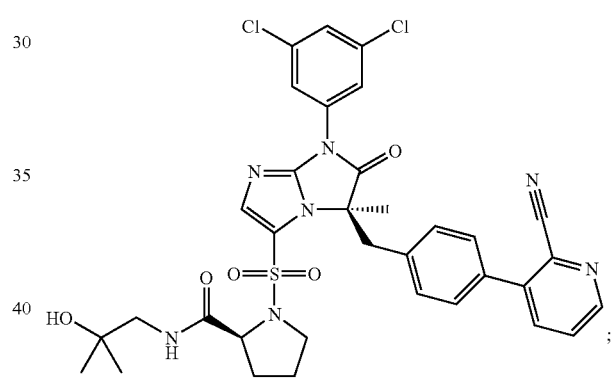

(S)-1-[(R)-5-[4-(2-Cyano-pyridin-3-yl)-benzyl]-7-(3,5-dichloro-phenyl)-5-methyl-6-oxo-6,7-dihydro-5H-imidazo[1,2-a]imidazole-3-sulfonyl]-pyrrolidine-2-carboxylic acid carbamoylmethyl-amide (707.1, M+1):

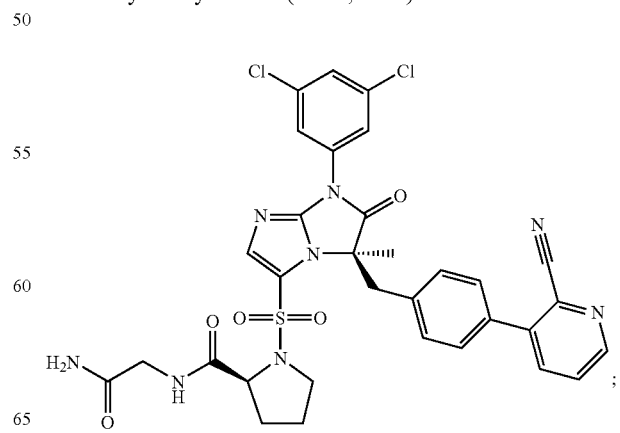

Description of Biological Properties

The biological properties of representative compounds of the formula I were investigated by way of the experimental protocol described below.

Assay to Determine Inhibition of LFA-1 Binding to ICAM-1

Purpose of Assay:

This assay protocol is designed to study the direct antagonism, by a test compound, of the interaction of the CAM, ICAM-1 with the Leukointegrin CD18/CD11a (LFA-1).

Description of Assay Protocol:

LFA-1 is immunopurified using the TS2/4 antibody from a 20 g pellet of human JY or SKW3 cells, utilizing a protocol previously described (Dustin, M. J.; et al., *J. Immunol.* 1992, 148, 2654-2660). The LFA-1 is purified from SKW3 lysates by immunoaffinity chromatography on TS2/4 LFA-1 mAb Sepharose and eluted at pH 11.5 in the presence of 2 mM $MgCl_2$ and 1% octylglucoside. After collection and neutralization of fractions from the TS2/4 column, samples are pooled and precleared with Protein G agarose.

A soluble form of ICAM-1 is constructed, expressed, purified and characterized as previously described (Marlin, S.; et al., *Nature,* 1990, 344, 70-72 and see Arruda, A.; et al., *Antimicrob. Agents Chemother.* 1992, 36, 1186-1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1 construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 µg/mL in Dulbecco's phosphate buffered saline with calcium and magnesium, additional 2 mM $MgCl_2$ and 0.1 mM PMSF (Diluting Buffer) in a 96-well plate for 30 min at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD 18 cytoplasmic tail in a 1:100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37° C., wells are washed as above and the substrate for the horse radish peroxidase is added to each well to develop a quantitative colorimetric signal proportional to the amount of LFA-1 bound to sICAM-1. Soluble ICAM-1 (60 µg/mL) is used as a positive control for inhibition of the LFA-1/ICAM-1 interaction. The lack of the addition of LFA-1 to the binding assay is used as a background control for all samples. A dose-response curve is obtained for all test compounds.

All compounds made in the above examples were tested in this assay and each found to have a $K_d < 10$ µM.

Assay to Determine Metabolism by Human Liver Microsomal Enzymes

Purpose of Assay:

This assay protocol is designed to measure the in vitro metabolism of test compounds by human liver microsomal enzymes. The data collected are analyzed to calculate a half-life ($t_{1/2}$, min) for test compounds.

Description of Assay Protocol:

The assay is performed in 50 mM potassium phosphate buffer, pH 7.4 and 2.5 mM NADPH. Test samples are dissolved in acetonitrile for a final assay concentration of 1-10 µM. Human liver microsomes are diluted in assay buffer to a final assay concentration of 1 mg protein/mL. A volume of 25 µL compound solution and 50 µL microsome suspension are added to 825 µL assay buffer. The preparation is incubated for 5 min in a 37° C. water bath. The reaction is started by the addition of 100 µL NADPH. Volumes of 80 µL are removed from the incubation mix at 0, 3, 6, 10, 15, 20, 40, and 60 min after the start of the reaction and added to 160 µL acetonitrile. The samples are shaken for 20 sec and then centrifuged for 3 min at 3000 rpm. A 200 µL volume of the supernatant is transferred to 0.25 mm glass fiber filter plates and centrifuged for 5 min at 3000 rpm. Injection volumes of 10 µL are typically added to Zorbax SB C8 HPLC columns with formic acid in water or acetonitrile at a flow rate of 1.5 mL/min. Percent loss of parent compound is calculated from the area under each time point to determine the half-life.

Compounds made in the above examples were tested in this assay and generally found to have a $t_{1/2} \geq 40$ minutes.

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g., as competitive inhibitors of intercellular ligand/receptor binding reactions involving CAMs and Leukointegrins. To be more specific, the compounds of the invention may be used to treat certain inflammatory conditions, including conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The compounds of the invention may also be used in treating asthma or as an adjunct to minimize toxicity with cytokine therapy in the treatment of cancers. In general these compounds may be employed in the treatment of those diseases currently treatable through steroid therapy.

Thus, another aspect of the invention is the provision of a method for the treatment or prophylaxis of the above-described conditions through the adminstration of therapeutic or prophylactic amounts of one or more compounds of the formula I.

In accordance with the method provided by the invention, the novel compounds of formula I may be administered for either a prophylactic or therapeutic purpose either alone or with other immunosuppressive or antiinflammatory agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered topically or by suppository.

Formulations

Compounds of the formula I can be formulated for therapeutic administration in a number of ways. Descriptions of several exemplary formulations are given below.

Example A

| Capsules or Tablets | | | |
|---|---|---|---|
| Example A-1 | | Example A-2 | |
| Ingredients | Quantity | Ingredients | Quantity |
| Compound of formula I | 250 mg | Compound of formula I | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of formula I is blended into a powder mixture with the premixed excipient materials as identified above with the exception of the lubricant. The lubricant is then blended in and the resulting blend compressed into tablets or filled into hard gelatin capsules.

Example B

| Parenteral Solutions | |
|---|---|
| Ingredients | Quantity |
| Compound of formula I | 500 mg |
| PEG 400 | 40% by volume |

-continued

| Parenteral Solutions | |
| --- | --- |
| Ingredients | Quantity |
| Ethyl Alcohol | 5% by volume |
| Saline | 55% by volume |

The excipient materials are mixed and then added to one of the compounds of formula I in such volume as is necessary for dissolution. Mixing is continued until the solution is clear. The solution then filtered into the appropriate vials or ampoules and sterilized by autoclaving.

Example C

| Suspension | |
| --- | --- |
| Ingredients | Quantity |
| Compound of formula I | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter one of the compounds of formula I is added and mixing is continued until the suspension is homogeneous. The suspension is then transferred into the appropriate vials or ampoules.

Example D

| Topical Formulation | |
| --- | --- |
| Ingredients | Quantity |
| Compound of formula I | 5% by weight |
| Tefose 63 | 13% by weight |
| Labrafil M 1944 CS | 3% by weight |
| Paraffin Oil | 8% by weight |
| Methylparaben (MP) | 0.15% by weight |
| Propylparaben (PP) | 0.05% by weight |
| Deionized water | q.s. to 100 |

The proper amounts of Tefose 63, Labrafil M 1944 CS, Paraffin oil and water are mixed and heated at 75° C. until all components have melted. The mixture is then cooled to 50° C. with continuous stirring. Methylparaben and propylparaben are added with mixing and the mixture is cooled to ambient temperature. The compound of formula I is added to the mixture and blended well.

We claim:

1. A method for treating inflammation or an inflammatory condition selected from adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis, granulocyte transfusion associated syndrome, psoriasis, organ/tissue transplant rejection, graft vs. host reactions, an autoimmune disease, asthma, or the toxic effects of cytokine therapy in a patient which comprises administering to said patient a therapeutically effective amount of a compound a compound of the formula I:

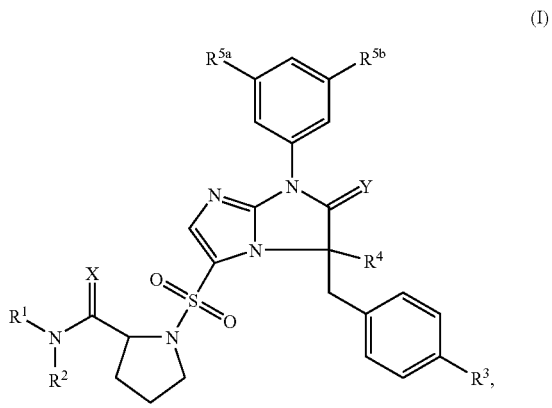

(I)

wherein:

$R^1$ and $R^2$ are each independently selected from the group consisting of:
(A) hydrogen, with the proviso that $R^1$ and $R^2$ are not both hydrogen atoms;
(B) —$R^{100}$, which is:
a straight or branched alkyl of 1 to 7 carbon atoms or cycloalkyl of 3 to 6 carbon atoms, which alkyl or cycloalkyl group is mono- or poly substituted with moieties independently selected from the group consisting of:
(i) oxo,
(ii) cyano,
(iii) halogen,
(iv) moieties of the formula —$COOR^6$, wherein $R^6$ is a hydrogen atom, a straight or branched alkyl of 1 to 7 carbon atoms or cycloalkyl of 3 to 6 carbon atoms,
(v) moieties of the formula —$OR^7$, wherein $R^7$ is a hydrogen atom, a straight or branched alkyl group of 1 to 7 carbon atoms or an acyl group of the formula —$COR^8$ wherein $R^8$ is a straight or branched alkyl group of 1 to 7 carbon atoms,
(vi) moieties of the formula —$NR^9R^{10}$, wherein $R^9$ and $R^{10}$ are each, independently selected from the group consisting of:
(a) hydrogen,
(b) straight or branched alkyl of 1 to 7 carbon atoms,
(c) acyl of the formula —$COR^{11}$ wherein $R^{11}$ is a straight or branched alkyl group of 1 to 7 carbon atoms, and
(d) groups of the formula —$COOR^{12}$ wherein $R^{12}$ is a straight or branched alkyl group of 1 to 7 carbon atoms,
or wherein $R^9$ and $R^{10}$ constitute a bridge consisting of 3-5 methylene groups or 2-4 methylene groups and one oxygen atom, such that the groups $R^9$ and $R^{10}$ together with the nitrogen atom between them form a heterocyclic ring, (vii) saturated heterocyclic groups, consisting of 3 to 5 methylene groups and one oxygen atom, wherein said heterocyclic groups are optionally mono- or disubstituted with moieties that are independently selected from the group consisting of:
  (a) oxo and
  (b) straight or branched alkyl of 1 to 3 carbon atoms; and
(viii) aryl, selected from the group consisting of:
  (a) furyl,
  (b) tetrazolyl and
  (c) thiophenyl;
(C) aryl, selected form the group consisting of:
  (i) biphenyl,
  (ii) phenyl which is mono- or di-substituted with moieties independently selected from the group consisting of —$NH_2$, and N-morpholino, and
  (iii) guinoliny; and
(D) unsaturated or partially saturated heterocyclic groups consisting of 2 to 3 carbon atoms, 1 to 2 nitrogen atoms, 0 to 1 sulfur atoms and 0 to 1 oxygen atoms wherein said heterocyclic group is optionally mono- or polysubstituted with one or more of the following moieties independently selected from the group consisting of:
  (i) oxo and
  (ii) straight or branched alkyl of 1 to 7 carbon atoms;
or wherein $R^1$ and $R^2$ constitute a saturated 3 to 5 methylene group bridge which together with the nitrogen atom between them form a heterocyclic ring, wherein said heterocyclic ring is mono- or disubstituted with moieties independently selected from the group consisting of:
(A) —OH,
(B) —COOH and
(C) —$CONH_2$;
$R^3$ is:
(A) aryl selected from the group consisting of pyridyl and pyrimidyl, wherein one or more hydrogen atoms of said aryl group are optionally and independently substituted with moieties selected from the group consisting of:
  (i) cyano,
  (ii) halogen and
  (iii) groups of the formula —$NR^{13}R^{14}$, wherein $R^{13}$ and $R^{14}$ are each, independently, hydrogen or straight or branched alkyl of 1 to 3 carbon atoms;
(B) trifluoromethoxy or,
(C) cyano;
$R^4$ is straight or branched alkyl of 1 to 3 carbon atoms;
$R^{5a}$ is Cl or $CF_3$;
$R^{5b}$ is Cl or $CF_3$;
X is an oxygen or a sulfur atom; and
Y is an oxygen or a sulfur atom;
or a pharmaceutically acceptable salt thereof.

2. The method of claim 1 wherein the condition to be treated is adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis or granulocyte transfusion associated syndrome.

3. The method of claim 1 wherein the condition to be treated is psoriasis, organ/tissue transplant rejection, graft vs. host reaction or an autoimmune disease.

4. The method of claim 1 wherein the condition to be treated is psoriasis.

5. The method of claim 1 wherein the condition to be treated is Raynaud's syndrome, autoimmune thyroiditis, dermatitis, multiple sclerosis, rheumatoid arthritis, insulin-dependent diabetes mellitus, uveitis, inflammatory bowel disease, Crohn's disease, ulcerative colitis or systemic lupus erythematosus.

6. The method of claim 1 wherein the condition to be treated is multiple sclerosis.

7. The method of claim 1 wherein the condition to be treated is asthma.

8. The method of claim 1 wherein the condition to be treated is the toxic effects of cytokine therapy.

* * * * *